12) United States Patent
Lippoff et al.

(10) Patent No.: US 10,832,823 B1
(45) Date of Patent: Nov. 10, 2020

(54) TRACKING AND AUTHENTICATION SYSTEM

(71) Applicant: AA DATABIT LLC, Brooklyn, NY (US)

(72) Inventors: Orrin Lippoff, Brooklyn, NY (US); Mladen Solar, Brooklyn, NY (US)

(73) Assignee: AA Databit LLC, Brooklyn, NY (US)

(*) Notice: Subject to any disclaimer, the term of this patent is extended or adjusted under 35 U.S.C. 154(b) by 111 days.

(21) Appl. No.: 15/825,846

(22) Filed: Nov. 29, 2017

Related U.S. Application Data

(60) Provisional application No. 62/432,186, filed on Dec. 9, 2016.

(51) Int. Cl.
G16H 80/00 (2018.01)
H04L 29/06 (2006.01)
H04L 29/08 (2006.01)

(52) U.S. Cl.
CPC ............ G16H 80/00 (2018.01); H04L 63/08 (2013.01); H04L 67/02 (2013.01)

(58) Field of Classification Search
None
See application file for complete search history.

(56) References Cited

U.S. PATENT DOCUMENTS

| 10,552,930 B1* | 2/2020 | Jordan-Nowe | G06Q 50/22 |
| 2002/0133386 A1* | 9/2002 | Chishti | G06Q 30/0201 705/7.29 |
| 2008/0046289 A1* | 2/2008 | Compton | G09B 23/28 705/3 |
| 2008/0046290 A1* | 2/2008 | Compton | G16H 40/20 705/3 |
| 2010/0106518 A1* | 4/2010 | Kuo | G16H 40/20 705/2 |
| 2011/0119075 A1* | 5/2011 | Dhoble | G06Q 50/22 705/2 |
| 2013/0271470 A1* | 10/2013 | Moore | G16H 10/60 345/440.1 |
| 2013/0282391 A1* | 10/2013 | Easterhaus | G16H 40/20 705/2 |
| 2013/0282397 A1* | 10/2013 | Easterhaus | G16H 40/20 705/3 |
| 2013/0325503 A1* | 12/2013 | Abrahams | G06Q 10/103 705/3 |
| 2014/0108030 A1* | 4/2014 | Tejeda-Monteagut | G06Q 10/1095 705/2 |
| 2014/0278480 A1* | 9/2014 | Baniameri | G16H 10/60 705/2 |
| 2014/0278550 A1* | 9/2014 | Pestka | G06F 19/00 705/3 |

(Continued)

Primary Examiner — Jerry B Dennison
(74) Attorney, Agent, or Firm — FisherBroyles, LLP

(57) ABSTRACT

An exemplary aspect includes a computer system that has a client-side presentation layer processor; a server-side service layer component comprising one or more API controllers, at least one repository pattern processor, and a data layer processor; and a back-end layer component comprising at least one SQL server and a cache. In various exemplary embodiments: (a) the presentation layer processor comprises one or more controllers; (b) the one or more API controllers provide application security and authentication; and (c) the data layer processor comprises at least one data access component.

14 Claims, 17 Drawing Sheets

(56) References Cited

U.S. PATENT DOCUMENTS

| | | | | |
|---|---|---|---|---|
| 2014/0304003 A1* | 10/2014 | Sethumadhavan | .... | G16H 10/60 |
| | | | | 705/3 |
| 2015/0278975 A1* | 10/2015 | Allen | ...................... | G16H 10/60 |
| | | | | 705/3 |
| 2015/0310173 A1* | 10/2015 | Coney | ................. | G06F 21/6245 |
| | | | | 705/3 |
| 2015/0356248 A1* | 12/2015 | Kogan | .................... | G16H 40/20 |
| | | | | 705/3 |
| 2016/0048660 A1* | 2/2016 | Lulias | ................... | G16H 10/60 |
| | | | | 705/3 |
| 2016/0140297 A1* | 5/2016 | Wisnicki | ................ | G16H 10/60 |
| | | | | 705/3 |
| 2016/0147972 A1* | 5/2016 | Mancine | ................ | G06Q 50/24 |
| | | | | 705/3 |
| 2016/0246926 A1* | 8/2016 | Morefield | ............... | G16H 10/60 |
| 2016/0321412 A1* | 11/2016 | Basri | ...................... | G06F 19/328 |
| 2017/0061077 A1* | 3/2017 | Cline | ...................... | G06F 19/00 |
| 2017/0103177 A1* | 4/2017 | Iliff | ........................ | G16H 40/20 |
| 2018/0108442 A1* | 4/2018 | Borve | ................... | G16H 30/20 |
| 2018/0182014 A1* | 6/2018 | Cheng | .................... | H04L 67/18 |

* cited by examiner

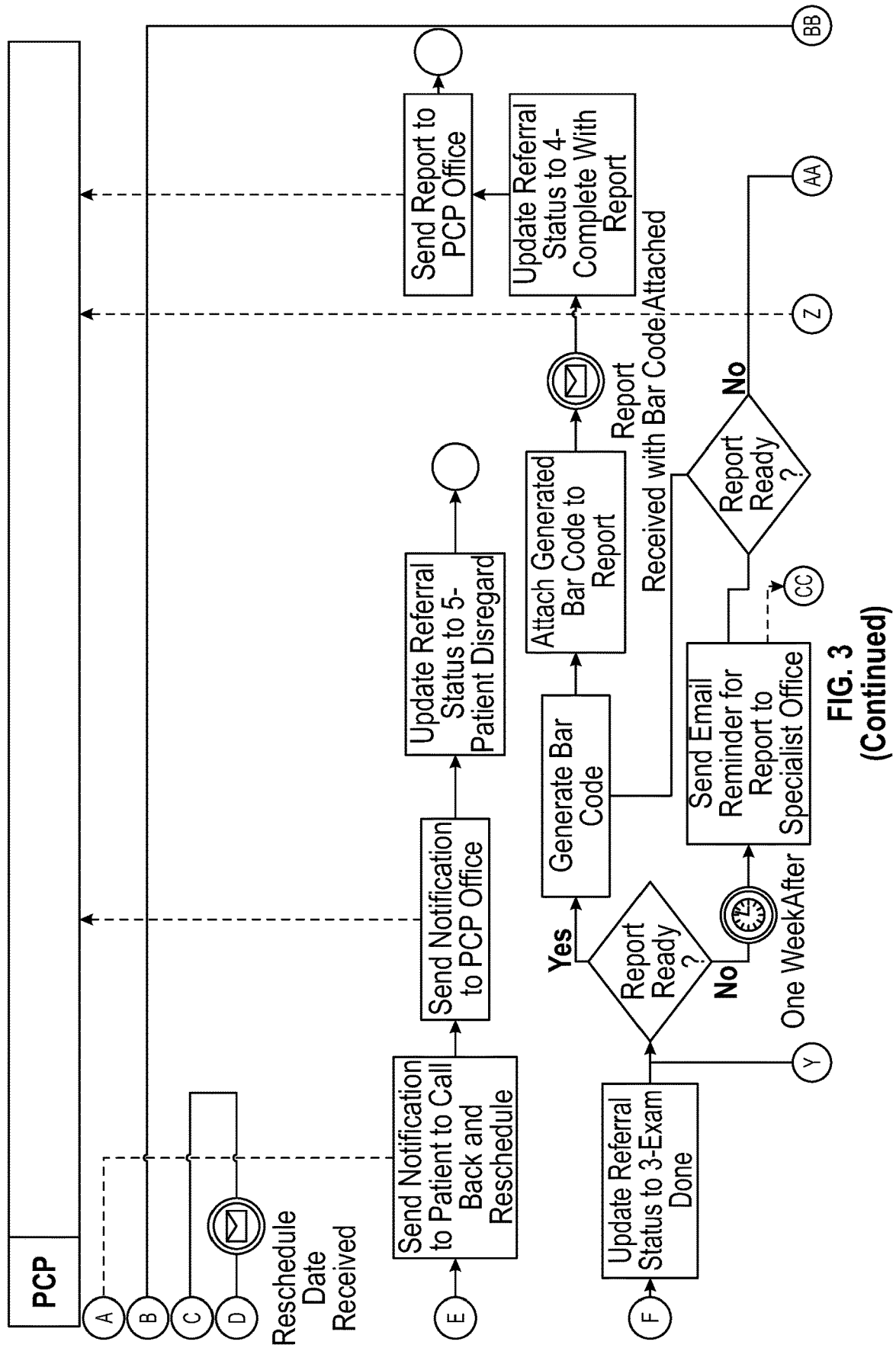

FIG. 9

| Name | Symbol | Description |
| --- | --- | --- |
| Task | | A task may be a unit of work – the job to be performed. It may be an atomic activity within a process flow. |
| Sub-process | | A collapsed sub-process may be a decomposable activity. It may be linked to another process diagram. |
| Exclusive Gateway | | Evaluates the state of the system process and, based on the condition, breaks the flow into one or more mutually exclusive paths |
| Parallel Gateway | | When used to split the sequence flow, all outgoing branches may be activated simultaneously. When merging parallel branches, it waits for all incoming branches to complete before triggering the outgoing flow. |
| Inclusive Gateway | | Breaks the process flow into one or more flows, when splitting, one or more branches may be activated based on branching conditions. When merging, it awaits all active incoming branches to complete. |
| Text Annotation | | Any object may be associated with a text annotation to provide additional documentation. |
| Message | | A message may be used to depict the contents of a communication between two participants. |
| Data Store | | A data store may be a place where the process may read or write data, e.g. a database or a filling cabinet. It persists beyond the lifetime of the process instance. |
| Start Event | | Start event that triggers a new process instance. |
| Start Message Event | | A process instance may be started on receipt of a message. |
| Start Conditional Event | | A process instance may be started based on changed system conditions or matching system rules |
| Intermediate Message Event | | This event reacts on the arrival of a message. |
| Intermedia Conditional Event | | Process execution may be delayed until a changed system condition or system rule matches. |
| End Event | | The end event typically marks the standard end of a process. |
| Sequence Flow | | Sequence flow defines the execution order of activities. |
| Message Flow | | Message flow symbolizes information flow across organizational boundaries. Message flow may be attached to pools, activities or message events. The order of message exchanges may be specified by combining message flow and sequence flow. |

TRACKING AND AUTHENTICATION SYSTEM

CROSS-REFERENCE TO RELATED APPLICATION

This application claims priority to U.S. Provisional Patent Application No. 62/432,186, filed Dec. 9, 2016, and entitled "Patient Referral and Hospital Discharge Tracking System," the entire contents of which are incorporated herein by reference.

INTRODUCTION

An exemplary aspect includes a computer system that has a client-side presentation layer processor; a server-side service layer component comprising one or more API controllers, at least one repository pattern processor, and a data layer processor; and a back-end layer component comprising at least one SQL server and a cache.

In various exemplary embodiments: (a) the presentation layer processor comprises one or more controllers; (b) the one or more API controllers provide application security and authentication; and (c) the data layer processor comprises at least one data access component.

One or more embodiments may comprise a system to track and improve referral coordination between primary-care providers and subspecialty physicians, and to provide hospitals and healthcare networks with access to referral patterns of associated providers.

In an embodiment, this system provides online access to a server-side system utilizing a secure portal, which enables primary care physicians to choose subspecialty referrals for patients from a list of pre-populated subspecialty physicians within a healthcare or hospital network.

In an embodiment, physicians may add new subspecialty physicians outside hospital or healthcare network, if a subspecialist may be not affiliated with an associated hospital or network; the added subspecialist may be considered a "leakage" referral, which may be identified to a hospital or healthcare network in a reporting module.

In an embodiment, the system also may provide notification and tracking of patients admitted to emergency departments or hospitals to primary care providers via secure email notification. Upon patient discharge, the system may contact the patient to schedule an appointment with a primary care or family practice provider, to reduce the likelihood of readmission for the same complaint within certain time period (e.g., 30 days).

Specific numerical values, time periods, codes, and messages described herein may be intended only to be illustrative, and do not limit the scope of the described system or claimed invention in any manner. Administrators and coordinators described herein may be software or hardware modules or circuits.

One or more embodiments of the system may track patient referral appointments on specific timeframes, in order to facilitate a subspecialist's report to a requesting primary care provider in a short time interval (configurable).

In an embodiment, the system automatically tracks a patient's appointment date and time, and thereafter contacts a subspecialty office via email to expedite subspecialty consult report generation for a primary care physician, in order to optimize patient care.

Additionally, in an embodiment, the system tracks patients who refuse to make an appointment with a subspecialist, or may be a no-show for a scheduled appointment. The system may notify the primary care provider automatically in such instances.

In an embodiment, the system accesses information from a subspecialty office on a secure portal, in order to retrieve notification if a patient missed or canceled an appointment.

In an embodiment, the system updates a primary care provider with updated information, which allows the primary care provider to reach out to patients based on importance of a subspecialty referral request, especially when importance of a requested referral may be paramount for disease management of a patient.

In an embodiment, the system provides a primary care provider with passive notifications via a system portal on a secure link to an affiliated hospital, when a patient may be admitted to an emergency room or hospital. Physicians may be notified on a mobile device in order to provide appropriate and timely treatment for patients that have been admitted to an emergency department ("ED") or hospital.

In an embodiment, the system tracks patients discharged from an ED or hospital through a secure link with an associated hospital. Upon discharge notification, a referral coordinator may reach out to a patient to schedule an appointment with the patient's primary care provider.

The system therefore reduces the likelihood of a patient's readmission to an emergency department or hospital, as a consequence of enhanced care provided through the system.

In an embodiment, the system identifies referral density patterns of subspecialty referrals based on primary care provider referral requests. This allows healthcare systems and hospitals to identify areas of need for subspecialists, based on those referral density patterns. The identification and subsequent placement of subspecialists in areas identified by the system may increase patient compliance with referral requests by providing patients the opportunity to see subspecialists in close proximity to their primary care physicians' offices.

The system thus provides several technical solutions for subspecialty referral and hospital discharge coordination, and enhances disease management while reducing risks associated with patient care for primary care physicians.

One object and feature of an embodiment is to allow physicians to access all outstanding referrals which have been requested utilizing a HIPAA secure portal. Additionally, utilization of the system may provide greater reassurance that a patient will complete a referral appointment requested from a primary care provider to a subspecialty physician.

It is a further object and feature of an embodiment to provide a system which may automatically follow-up on a patient's appointment with a subspecialist to verify that the appointment has been completed, by updating a primary care physician who requested the referral. The system also may update a primary care physician if a patient refuses a referral or was a no-show.

It is a further object and feature of an embodiment to provide a system that enables authorized persons utilizing the system to track referral patterns within a healthcare network, to ascertain referral density patterns based on primary care physician requests, patient needs, and distances required for patients to travel to obtain referral appointments.

It is a further object and feature of an embodiment to enable healthcare and hospital networks to better align primary care referrals for their patients within a close geographic proximity to primary care offices. In addition the system may enhance connectivity linkage between primary-care providers and subspecialty physicians within the same healthcare or hospital network, in order to enable improved exchange of medical information among primary care providers and subspecialty physicians.

It is a further object and feature of an embodiment for the system to notify primary care and family based physicians when patients may be admitted to an emergency department or a hospital within a healthcare network. Primary-care physicians may be immediately notified upon registration of their patients via secure notification to smart phone or email devices.

It is a further object and feature of an embodiment for the system to notify primary care physicians when patients may be discharged by a hospital or healthcare network and to provide tracking of patient's status until discharge. Upon discharge, patients may be contacted by the system to schedule patients for appointments with primary care providers within, say, 48 hours of hospital discharge.

This system may maintain tracking of all hospital and emergency room admissions within a healthcare network, and provide authorized personnel within a healthcare network the ability to track admissions to emergency rooms and hospitals of patients of primary care and family practitioners.

In an embodiment, the system reduces likelihood of re-admittance of patients to emergency rooms or hospitals through its coordinated effort to align patients with their primary care providers, by coordinating appointments within, for example, a 30 day window after discharge and by contacting patients within, for example, 48 hours of discharge.

BRIEF DESCRIPTION OF THE DRAWINGS

The present invention will be better understood when considered in view of the attached drawings, in which like reference characters indicate like parts, The drawings, however, are presented merely to illustrate certain exemplary embodiments without limiting the invention in any manner whatsoever.

FIG. 9 defines symbols used in the other drawings.

DETAILED DESCRIPTION OF SELECT EXEMPLARY EMBODIMENTS

Figure 1:
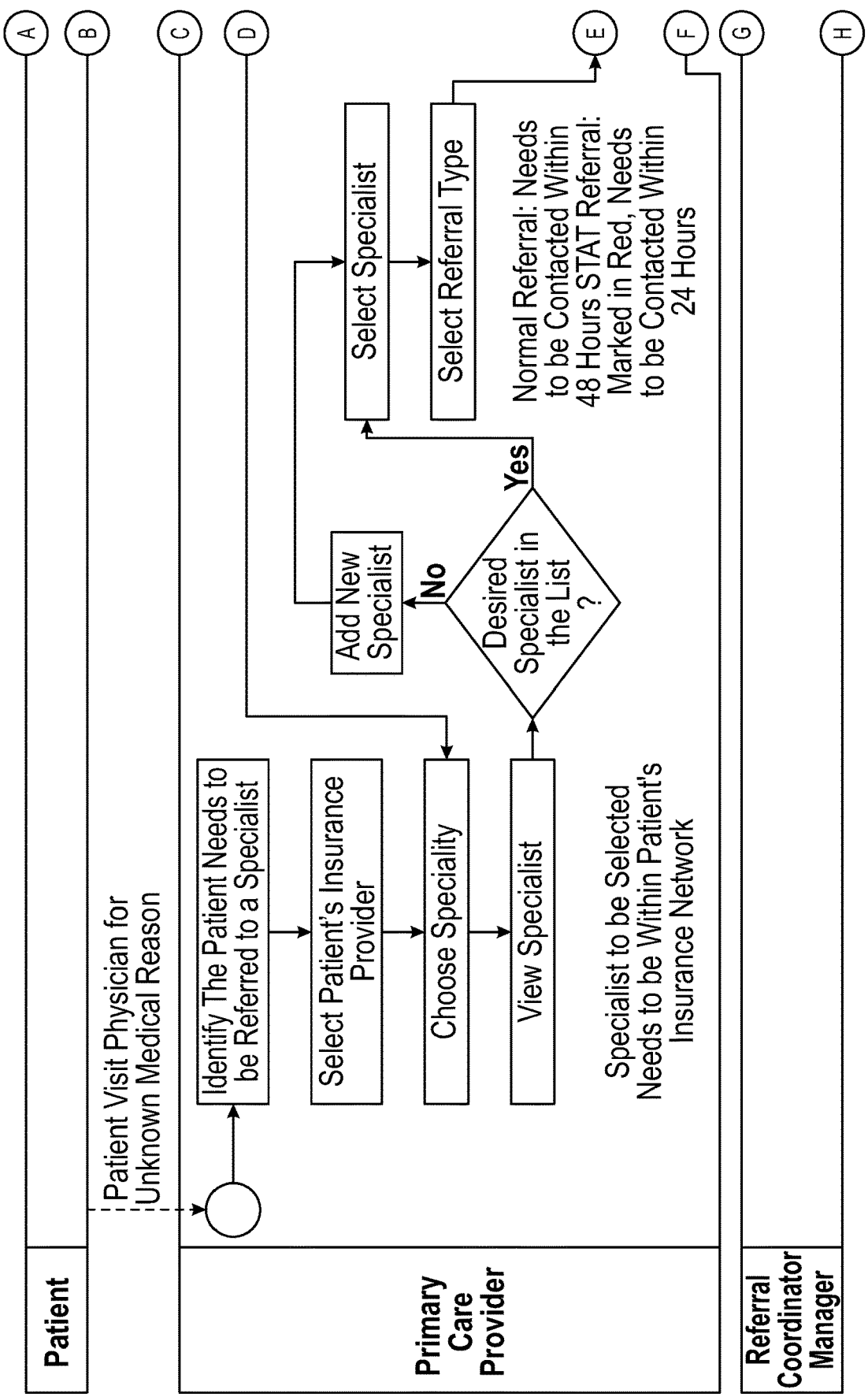
FIG. 1 is a workflow diagram depicting a Submit New Referral Process of an exemplary embodiment.
Figure 1:
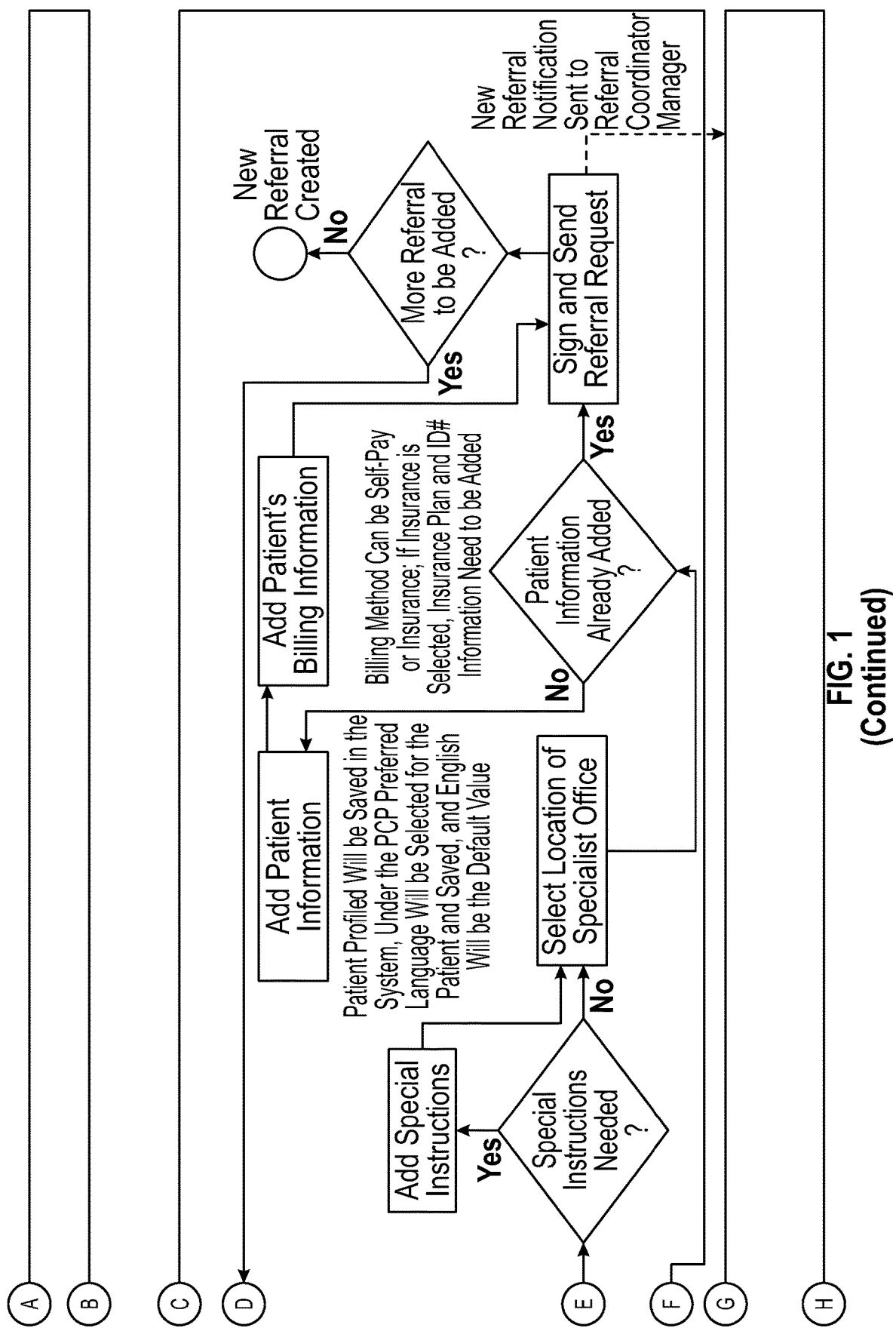

The following text sets forth a broad description of numerous different embodiments of the present disclosure. The description is to be construed as exemplary only and does not describe every possible embodiment since describing every possible embodiment would be impractical, if not impossible. It will be understood that any feature, characteristic, component, composition, ingredient, product, step or methodology described herein can be deleted, combined with or substituted for, in whole or part, any other feature, characteristic, component, composition, ingredient, product, step or methodology described herein. Numerous alternative embodiments could be implemented, using either current technology or technology developed after the filing date of this patent, which would still fall within the scope of the claims. All publications and patents cited herein are incorporated herein by reference.

An embodiment comprises a system of referral management services that provides access points between primary-care providers, subspecialists, and one or more hospital or healthcare networks.

This system may provide referral management resources to enable scheduling of patients as requested by primary care providers to subspecialists within a provider network of affiliated physicians, in order to increase the percentage of completed referrals by patients.

This system may facilitate requested subspecialty appointments by primary care provider by acting as a proxy center with the ability to provide requesting provider access through a secure portal to maintain up-to-date information and control of requested referrals The system may generate monthly, quarterly, and/or yearly reports in order to enable primary care physicians and health-care or hospital networks to identify gaps in areas where subspecialties may be required, by analyzing referral density per requests of primary-care providers with regard to subspecialty referrals and based on geographic locations of subspecialty physicians from primary care offices.

The system may increase physician and patient compliance with completing requested referral appointments to subspecialists.

Through utilization of a secure portal the system may track emergency room and hospital admissions in order to provide physician notifications. In addition, the system may provide scheduling of patient appointments upon discharge, with primary care provider, in order to ensure appropriate follow-up care after hospital discharge and to reduce the possibility of readmission within a 30 day window, in order to improve overall disease management of patients.

System Processes: for each system process, the following elements may include:
  Purpose/Scope: this section may provide a description of the purpose and scope of the entire system and system process.
  Workflow Diagram: this section may include a visual diagram of the workflow, indicating the relationship between activities in the process.
  Activity Description: this section may describe each of the activities of the system and system processes.
  Inputs: inputs may be deliverables that a person responsible for initiating the process receives in either physical or electronic form. (A deliverable could be an email, a document, an updated database entry, a fax, etc.)
  Outputs: this section may provide an explanation of the process's outputs or deliverables.
  Roles & Responsibilities: this section may describe the roles and responsibilities; it may be also be possible that one person/module/circuit may fulfill more than one role within a process—or that multiple people modules/circuits may share the same role.

System Rules: this section may include a list of relevant system rules and reference the steps from the Activity description section in which they may be enforced.

System Requirement: this section may include a list of system requirements for the system area discussed.

System Description and Functional Requirement: may list all the desired system features with functional requirements. Notation: The workflow diagrams included in this description use System Process Model and Notation (BPMN) 2.0, which is an international standard for system process modeling. The symbols depicted in FIG. 9 may be used.

Embodiments described herein are intended to provide one or more of the following improvements:

Better Data Quality: The system provides an integrated data platform that seamlessly connects different data sources and workflows. The net result is that the system may provide a single source of data that is real time, up-to-date and accurate.

Automation: The system may enable easier tracking of referrals, ER/hospital admissions, communication, notes, notifications, alerts and key system process artifacts—thereby reducing the amount of duplicate work, manual labor, and unnecessary errors produced during day-to-day operations.

Better Reporting: The system may record and report on operations better, to generate desired reports based on criteria defined, as well as based on a centralized data set.

Knowledge Generation: The system improve the type of information available. The system moves beyond information capture and enables knowledge generation—helping an organization make strategic decisions, identify trends in services provided, and uncover new areas of growth.

In addition to the above stated features, the system is HIPAA Compliant. The passage of the Health Insurance Portability and Accountability Act (HIPAA) by Congress in 1996 has complicated traditional referral request systems. HIPAA establishes rigorous standards for protecting sensitive patient information.

The Final Rule on Security Standards was issued on Feb. 20, 2003. It took effect on Apr. 21, 2003 with a compliance date of Apr. 21, 2005 for most covered entities and Apr. 21, 2006 for "small plans". The Security Rule complements the Privacy Rule. While the Privacy Rule pertains to all Protected Health Information (PHI) including paper and electronic, the Security Rule deals specifically with Electronic Protected Health Information (EPHI). It lays out three types of security safeguards required for compliance: administrative, physical, and technical. For each of these types, the Rule identifies various security standards, and for each standard, it names both required and addressable implementation specifications. Required specifications may be adopted and administered as dictated by the Rule. Addressable specifications may be more flexible. Individual covered entities may evaluate their own situation and determine the best way to implement addressable specifications. Some privacy advocates have argued that this "flexibility" may provide too much latitude to covered entities. The standards and specifications may be as follows:

Administrative Safeguards—policies and procedures designed to clearly show how the entity may comply with the act Covered entities (entities that may comply with HIPAA requirements) may adopt a written set of privacy procedures and designate a privacy officer to be responsible for developing and implementing all required policies and procedures.

The policies and procedures may reference management oversight and organizational buy-in to compliance with the documented security controls.

Procedures may clearly identify employees or classes of employees who may have access to electronic protected health information (EPHI). Access to EPHI may be restricted to only those employees who have a need for it to complete their job function.

The procedures may address access authorization, establishment, modification, and termination.

Entities may show that an appropriate ongoing training program regarding the handling of PHI may be provided to employees performing health plan administrative functions.

Covered entities that out-source some of their system processes to a third party may ensure that their vendors also have a framework in place to comply with HIPAA requirements. Companies typically gain this assurance through clauses in the contracts stating that the vendor may meet the same data protection requirements that apply to the covered entity. Care may be taken to determine if the vendor further out-sources any data handling functions to other vendors and monitor whether appropriate contracts and controls may be in place.

A contingency plan may be in place for responding to emergencies. Covered entities may be responsible for backing up their data and having disaster recovery procedures in place. The plan may document data priority and failure analysis, testing activities, and change control procedures.

Internal audits play a key role in HIPAA compliance by reviewing operations with the goal of identifying potential security violations. Policies and procedures may specifically document the scope, frequency, and procedures of audits. Audits may be both routine and event-based.

Procedures may document instructions for addressing and responding to security breaches that may be identified either during the audit or the normal course of operations.

Physical Safeguards—controlling physical access to protect against inappropriate access to protected data Controls may govern the introduction and removal of hardware and software from the network. (When equipment may be retired it may be disposed of properly to ensure that PHI may be not compromised.)

Access to equipment containing health information may be carefully controlled and monitored.

Access to hardware and software may be limited to properly authorized individuals.

Required access controls consist of facility security plans, maintenance records, and visitor sign-in and escorts.

Policies may be required to address proper workstation use. Workstations may be removed from high traffic areas and monitor screens may not be in direct view of the public.

If the covered entities utilize contractors or agents, they too may be fully trained on their physical access responsibilities.

Technical Safeguards—controlling access to computer systems and enabling covered entities to protect communications containing PHI transmitted electronically over open networks from being intercepted by anyone other than the intended recipient.

Information systems housing PHI may be protected from intrusion. When information flows over open networks, some form of encryption may be utilized. If closed systems/networks may be utilized, existing access controls may be considered sufficient and encryption may be optional.

Each covered entity may be responsible for ensuring that the data within its systems has not been changed or erased in an unauthorized manner.

Data corroboration, including the use of check sum, double-keying, message authentication, and digital signature may be used to ensure data integrity.

Covered entities may also authenticate entities with which they communicate. Authentication consists of corroborating that an entity may be who it claims to be. Examples of corroboration include: password systems, two or three-way handshakes, telephone callback, and token systems.

Covered entities may make documentation of their HIPAA practices available to the government to determine compliance.

In addition to policies and procedures and access records, information technology documentation may also include a written record of all configuration settings on the components of the network because these components may be complex, configurable, and always changing.

Documented risk analysis and risk management programs may be required. Covered entities may carefully consider the risks of their operations as they implement systems to comply with the act. (The requirement of risk analysis and risk management implies that the act's security requirements may be a minimum standard and places responsibility on covered entities to take all reasonable precautions necessary to prevent PHI from being used for non-health purposes.)

System Processes Description—Exemplary Embodiments

A Submit New Referral Process may be created to describe how the new referral may be created for a Patient, when they visited their Primary Care Provider (PCP) and needed a Specialist. See FIG. 1.

Activity Description

A Submit New Referral Process may begin when a Patient visits his Primary Care Provider (PCP), and the PCP decides that a Referral may be needed for the Patient.

In order to create a new Referral, the PCP enters the Patient's information, including Insurance and Insurance Provider information, so that Specialists within the Insurance Provider's network may be narrowed and listed.

Based on the Insurance provider defined for the Patient and the selected Specialty for the Referral, the list of Specialists will be filtered, and the listed Specialists will be within the Patient's insurance coverage. If no specialist is located under the Patient's insurance, the requesting office places the referral in a holding status until the physician approves an alternative specialist for the patient in order to complete the referral request. The system will identify that no specialists are currently loaded that meet the requirement for a particular patient's insurance. The PCP requests the Provider to choose a Specialist for the referral if a physician is not already loaded within the software.

After a Specialist is selected, the PCP enters the details of the Referral, including Referral Type and special instructions/patient history if applicable.

If this is an existing Patient, the patient information may be already in profile, which may also be updated, including the Patient's billing information—either to be paid by Insurance or by patient; if this is a new Patient, a new Patient profile may be added and saved.

At this point, the Referral may be signed and created; new Referral notifications may be sent to a Referral Coordinator Manager.

After one Referral is created for the Patient, the system may allow the PCP to create more Referrals for the same Patient by redirecting back to "Choose Specialty".

Inputs for the Submit New Referral Process may include:
The Patient's Insurance information
The pre-defined Specialties list
Insurance Provider's network coverage information for Specialists
The Specialist's detailed information, such as Locations
The Patient's detailed information, which may either be entered for new Patient or selected from existing Patient profiles
The Patient's billing information, which may either be Insurance pay or self-pay Outputs for the Submit New Referral Process may include the newly created Referral record(s) with unique tracking identifier code(s), and notifications sent to a Referral Coordinator Manager, which may then assign the new created Referral during the Coordinate Referral Process.

Roles & Responsibilities involved in this process may include the following:
Patient, who goes to PCP for unknown medical reason
Primary Care Provider (PCP), who decides that a referral may be needed for the Patient and submits the Referral request in the system
Referral Coordinator Manager, which may receive notifications for new Referral

TABLE 1

Exemplary System Rules Description

There may be two types of Networks:
  Healthcare System Network: this may be used to track whether the Specialist may be In- or Out-of- the Healthcare System's network
  Insurance Network: this may be used to identify a Specialist that may be In- or Out-of- Patient's Insurance network
PCP (Primary Care Provider) may be associated with only one Hospital (at a specific address), or none as individual PCP.
Specialist may be In- or Out- the selected Healthcare System's network.
Patient may see PCP first to get referral to Specialist.
Each Patient may be attached with one PCP, only that PCP has access to this Patient's data.
Patient may be referred to more than one Specialist at one time.
Each Referral may have a unique Referral ID, even when multiple Referrals are created for one Patient at one time.
Specialist may be selected based on Patient's insurance coverage.

TABLE 2

Exemplary Process Requirements Description

Healthcare System and Hospital may be added as a client account, with Healthcare System Admin User created and assigned.
PCP may be attached to only one Hospital.
PCP office staff may be able to submit Referral on behalf of the selected PCP.

TABLE 2-continued

Exemplary Process Requirements Description

PCP office staff may be associated with location, and be able to submit Referral for PCP(s) in the same location.
Specialist may be affiliated with at least one Healthcare System.
Patient profiles may be added under PCP, and PCP users only have access to Patients attached to them.
Patient's insurance information to be collected.
Patient's insurance information may be used to narrow down Specialists that may be within Patient's insurance network.
Specialty may be defined.
Selection of Specialist may depend on defined Insurance and Specialty.
PCP may be able to indicate whether the Specialist may be with In- or Out-of- the network of the PCP's Hospital.
Report may be generated to show referred Specialists and Hospital network information.
New Specialist may be added.
Patient's preferred language may be specified.
Patient's Diagnosis information may be defined for a Referral record.
Patient's billing information may be specified.
Special instruction may be added for new Referral.
Multiple Referral records may be added for one Patient at once.
Notifications may be sent to Referral Coordinator Manager when a new Referral is created.

Figure 2:
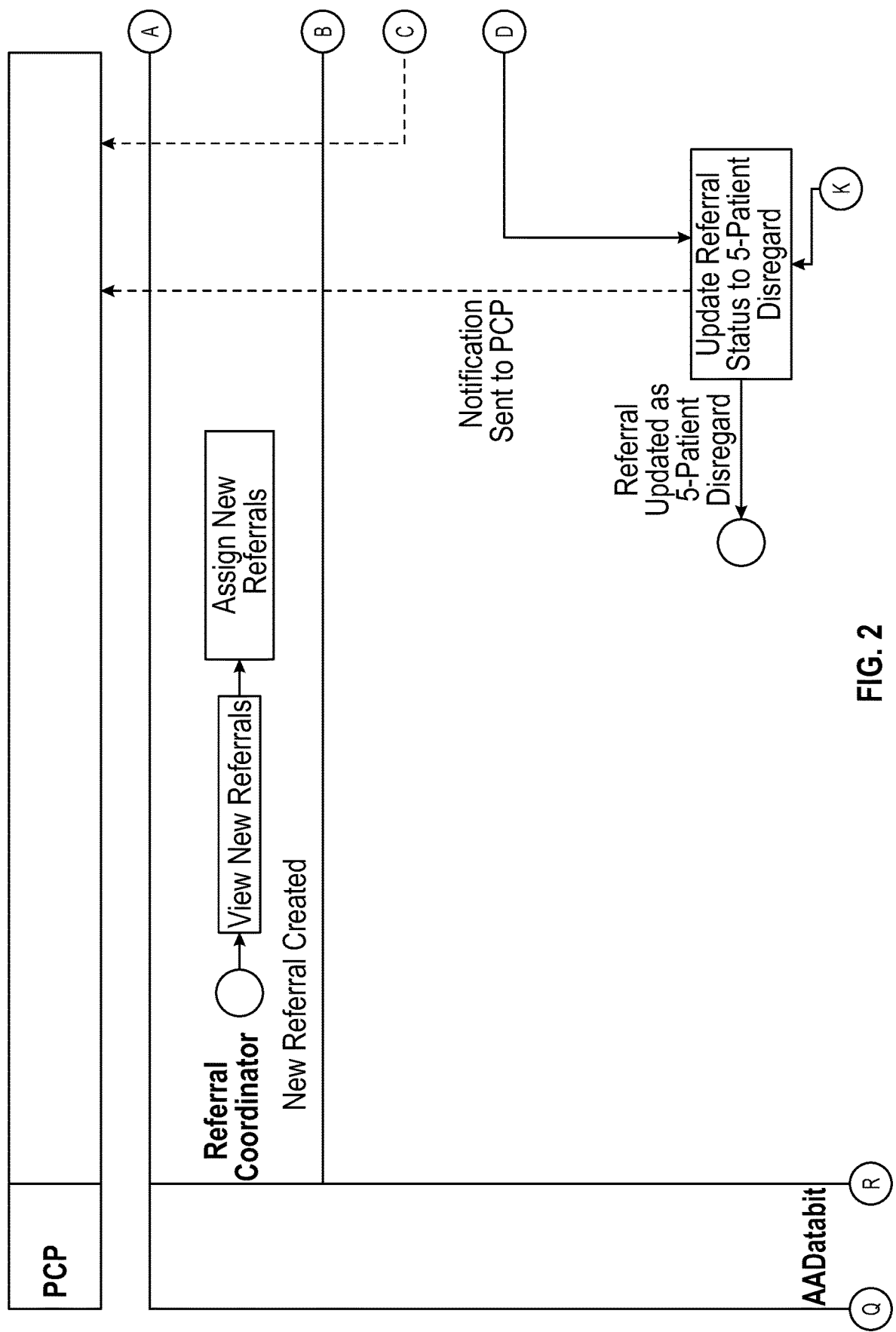
FIG. 2 is a workflow diagram depicting a Coordinate Referral Process of an exemplary embodiment.
Figure 2:
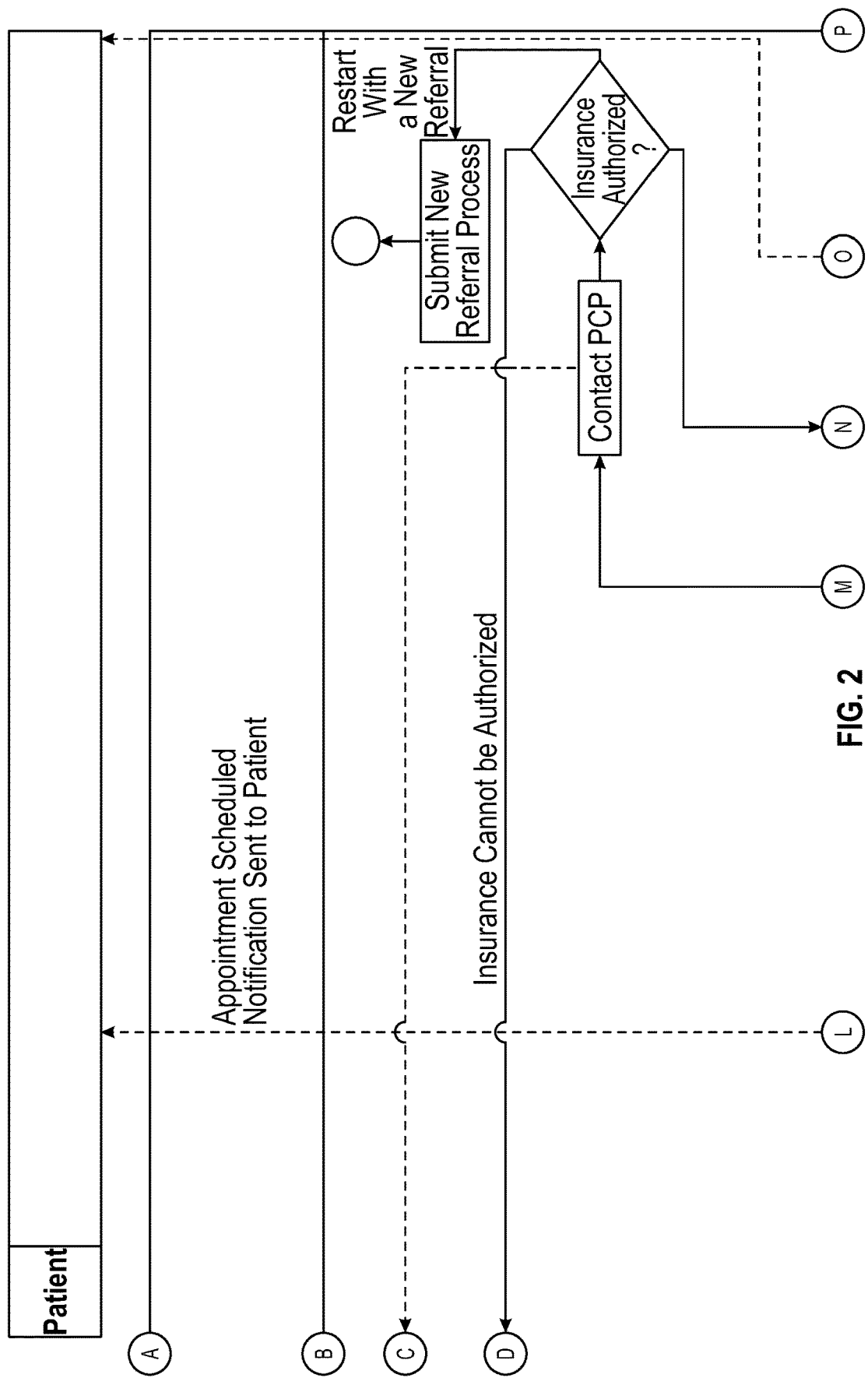
Figure 2:
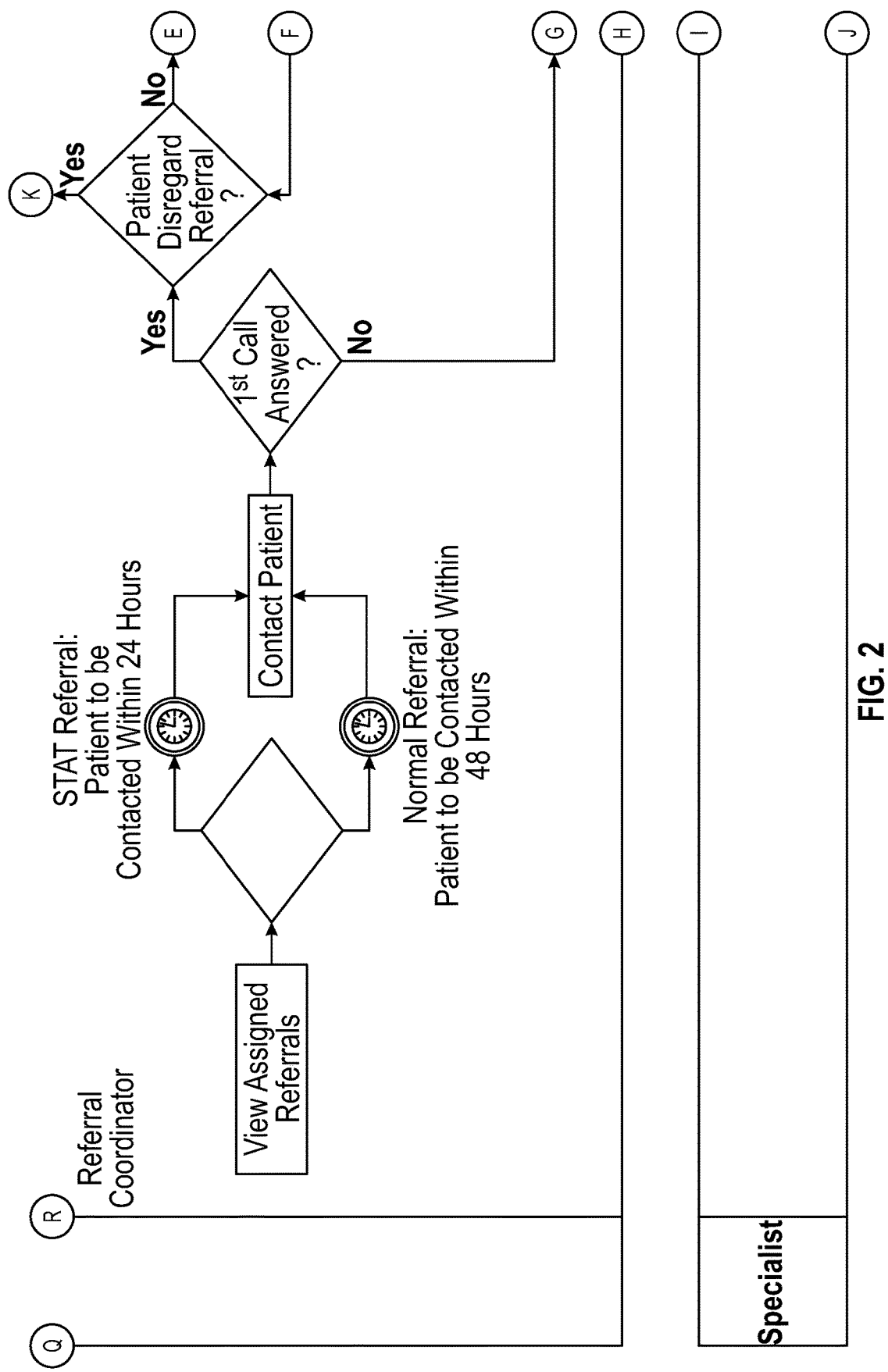
Figure 2:
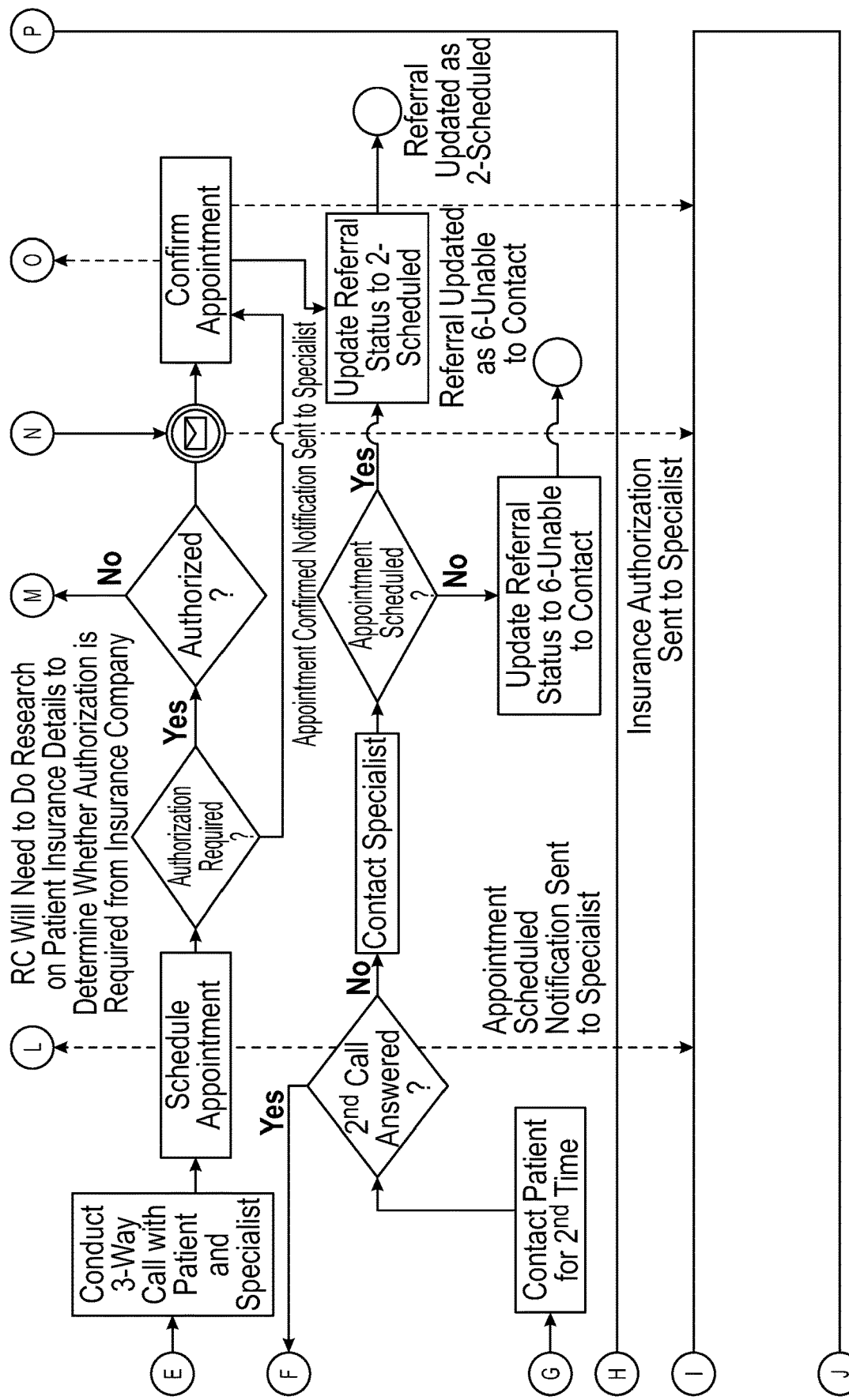

An exemplary Coordinate Referral Process may be triggered when the new Referral is created after a Submit New Referral Process, and enables a Referral Coordinator to helps a Patient and Specialist to schedule an appointment. See FIG. 2.

The Coordinate Referral Process may be triggered when a new Referral is created after a Submit New Referral Process, which may send a notification to a Referral Coordinator Manager.

Upon receiving new Referral creation notifications, a Referral Coordinator Manager may assign each new Referral created to a Referral Coordinator.

Once a new referral is assigned, the Referral Coordinator may contact the individual Patient based on Referral Type:
  I. Normal Referral: Patient to be contacted within 48 hours of submission.
  II. STAT Referral: Patient to be contacted within 24 hours of submission.

If the Patient is contacted by the system, the Patient may disregard the Referral, in which case a Referral status on the system may be changed to "5—Patient Disregard", and the system may send a notification to the PCP office automatically by end of day; otherwise, when the appointment has been scheduled, notifications may be sent to the Patient and the Specialist, and the scheduled date may be added to the Patient's calendar.

Once the appointment is scheduled: if no authorization is required, the appointment may be confirmed directly; otherwise, if authorization is required, the appointment may only be confirmed after the authorization may be generated from the Insurance company. Once the appointment may be scheduled and confirmed, the Referral status may be changed to "2—Scheduled" with sub status as "Confirmed". When the appointment has been confirmed, notifications may be sent to the Patient and the Specialist.

In case authorization is required but denied by the Insurance company, the system may contact the PCP, which may result in the following three scenarios:
  I. Insurance authorization generated—this may lead to the appointment confirmation.
  II. Insurance not authorized—in this case, the Referral status may be changed to "5—Patient Disregard" and the system may send a notification to the PCP office automatically.
  III. A new Referral may be needed, with another Specialist selected, which may trigger a Submit New Referral Process.

If the $1^{st}$ call is NOT picked up by the Patient, the Referral Coordinator or system may call the Patient for a $2^{nd}$ time; if the $2^{nd}$ call is picked up, the system may perform the same steps when the $1^{st}$ call is picked up, otherwise, the system may contact the Specialist to find out more details. If after the second attempt there is no patient contact; the system will notify the patient via a text message and then notify the PC if no contact with patient was possible.

If the Referral Coordinator/system determines that the appointment has already been scheduled, the Referral status may be changed to "2—Scheduled". Otherwise, the Referral status may be changed to "6—Unable to Contact".

Inputs for a Coordinate Referral Process may include:
The newly created Referral request
Insurance company and Insurance plan policy
Outputs for the Coordinate Referral Process may include:
Updated Referral status
Notifications when Referral status gets updated
Roles & Responsibilities involved in this process may include the following:
  Referral Coordinator Manager, whose responsibility may be to assign the new created Referrals to Referral Coordinators.
  Referral Coordinator, whose responsibility may be to contact Patients, and coordinate among Patients, Specialists, and PCPs to schedule a Referral appointment.

TABLE 3

Process Rules Description

Referral needs to be assigned first then be worked on.
There may be two types of Referral:
  Normal Referral: Patient may be contacted within 48 hours of submission.
  STAT Referral: Patient may be contacted within 24 hours of submission.
Depends on Insurance provider and Insurance plan, some Referral Appointment requires Insurance provider's authorization.

TABLE 4

System Requirement Description

Referral Coordinator Manager may assign new Referral to Referral Coordinator.
Notifications may be sent to a Referral Coordinator when new Referral may be assigned.
When Referral Coordinator contacts Patient for appointment, if the 1st call was not answered, call needs to be made in 2 days.
Referral Coordinator may conduct 3-way call between Patient and Specialist to schedule the appointment; and once appointment scheduled, notifications may be sent to both the Patient and the Specialist.
Notifications may be sent via Text message if cell phone may be provided, or Email if email address may be provided.
Appointment schedule notifications may be added to Patient or Specialist's calendar.
Reminders may be sent [X] days (configurable) before the scheduled date.
Appointment may be confirmed, and notifications may be sent to both Patient and Specialist when confirmed.
When Referral may be scheduled, the Referral status may be automatically changed to "2 - Scheduled".
When Referral is confirmed, the Referral sub status may be automatically changed to "Confirmed".
For Referral requires Insurance Authorization, system may automatically update sub status to "Confirmed" only after Authorization document uploaded.

TABLE 4-continued

System Requirement Description

Once Referral is Scheduled and Confirmed, the full Referral script may be auto faxed to Specialist.
Referral status may be updated to "5 - Patient Disregard" when the Patient disregards the call and referral.
Referral status may be updated to "6 - Unable to Contact" when the Patient is not contacted for the referral.
Daily report may be sent to PCP office by end of day, when the Referral status is changed to "5 - Patient Disregard" and "6 - Unable to Contact".

Figure 3:
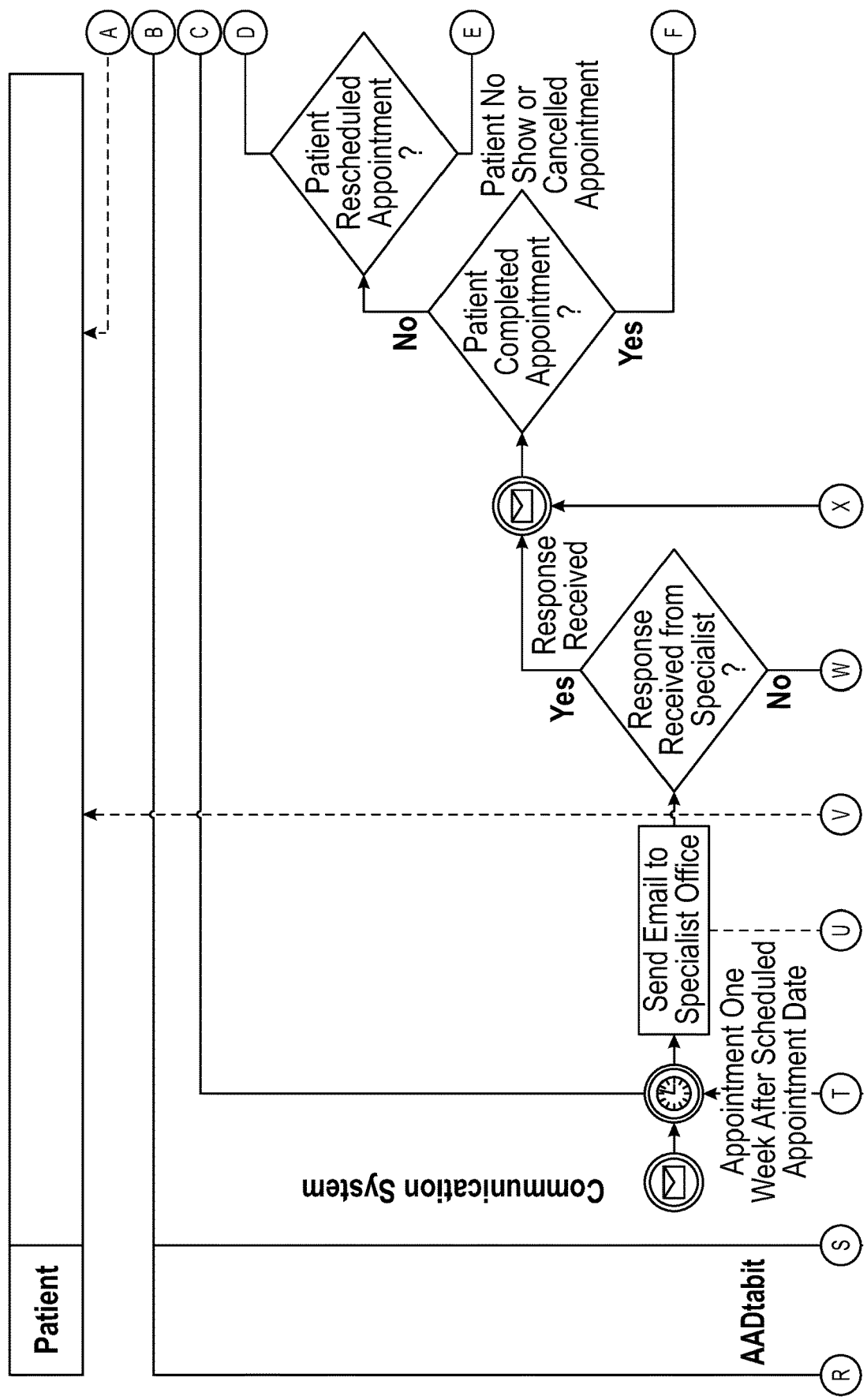
FIG. 3 is a workflow diagram depicting a Follow Up Referral Appointment Process of an exemplary embodiment.
Figure 3:
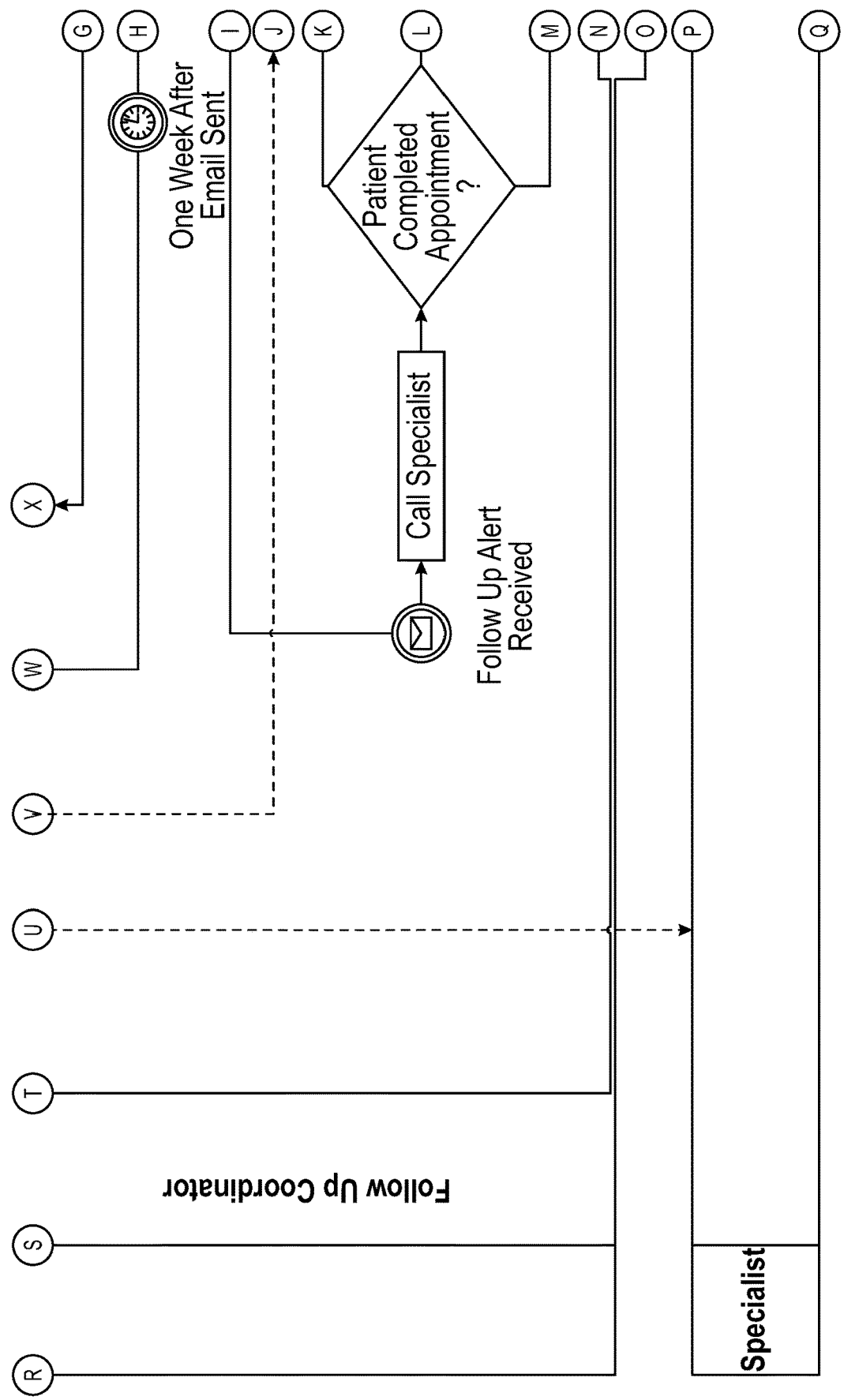
Figure 3:
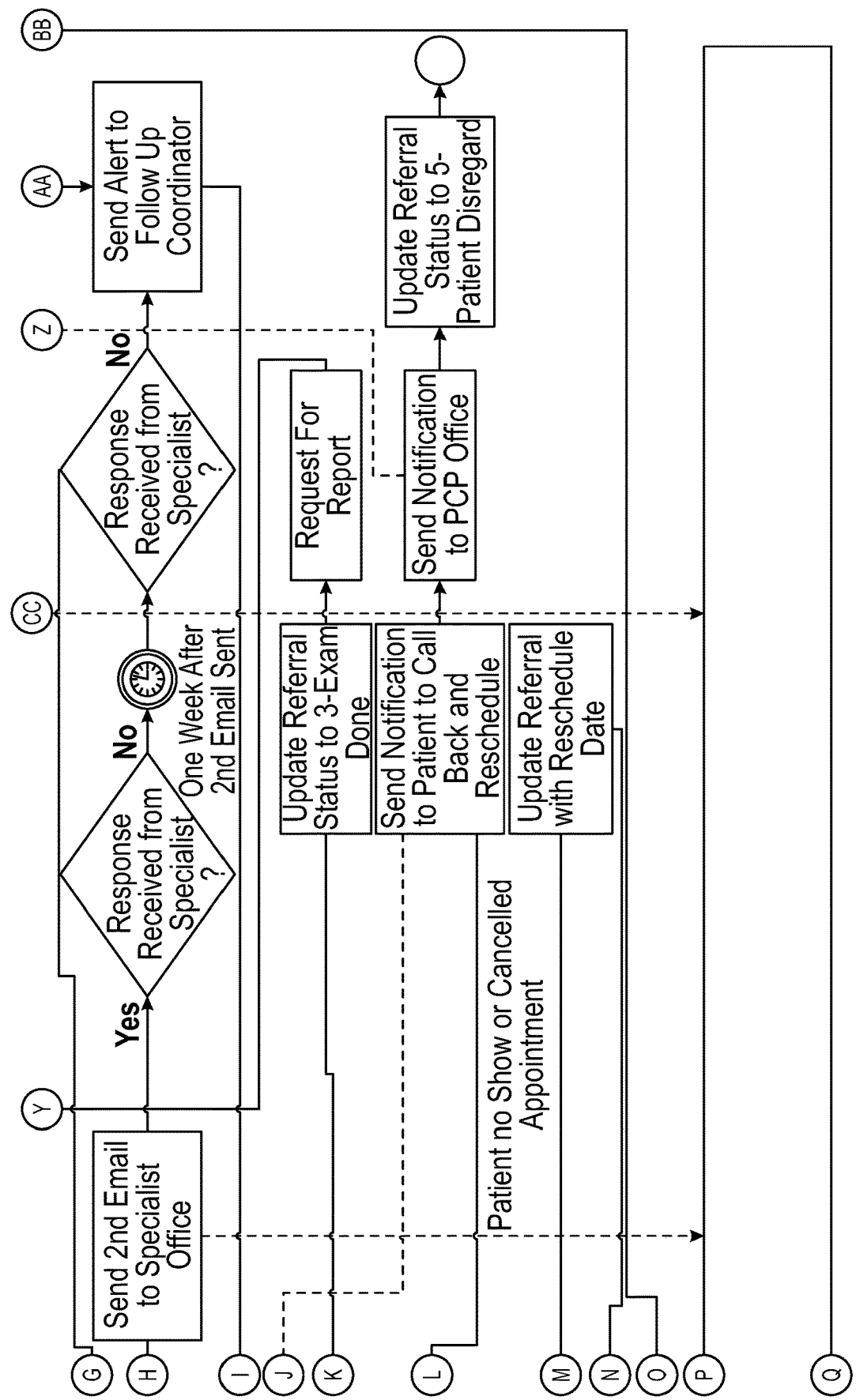

A Follow Up Referral Appointment Process may begin after the Referral is scheduled, and the system may send follow up emails to get a Report and then complete the Referral. See FIG. 3.

A Follow Up Referral Appointment Process may be triggered when an Appointment is scheduled. One week after the scheduled date, the system may send an email to the Specialist Office to follow up, including a link, clicking which may present the following emailed questions which may be used to query the Specialist to answer and submit:
  I. Has Patient Completed the Appointment?—Yes or No
    i. If "Yes", go to question II
    ii. If "No", select from the following conditions:
      a. Patient has rescheduled Appointment—if selected, reschedule date needs to be entered
      b. Patient was No Show
      c. Patient Canceled Appointment
  II. Is the Report Ready?—Yes or No If the Patient has completed the Appointment and the Report is ready, the system may generate a unique bar code and send it to the Specialist office, which may then attach the bar code to the Report and send the Report to the system. Upon receiving the Report, the system may read the unique bar code and attach the Report to the corresponding Referral, as well as sent the Report to the PCP Office automatically, with Referral status changed to "4—Complete with Report".

If the Patient has completed the Appointment but the Report is NOT ready, system may send a Reminder notification one week after asking for the Report. If the Report is still not received by that time, system may send an alert to a Follow Up Coordinator, who may then contact the Specialist to find out more details.

If the Patient has NOT completed the Appointment, and:
  a. Patient has rescheduled Appointment: The Specialist may report the reschedule date, which may restart the process and trigger a follow up Email one week after the rescheduled date.
  b. Patient was No Show: System may send notifications to Patient to reschedule the Referral with the system, and the system may also send notifications to the PCP office, with Referral status changed to "5—Patient Disregard" with "No Show" noted.
  c. Patient Cancelled Appointment: System may send notifications to Patient to reschedule the Referral with the system, and the system may also send notifications to the PCP office, with Referral status changed to "5—Patient Disregard" with "Cancellation" noted.
  d. Patient has NOT rescheduled Appointment: System may send notifications to Patient to reschedule the Referral with the system, and the system may also send notifications to the PCP office, with Referral status changed to "5—Patient Disregard".

On the other hand, if NO response is received from the 1$^{st}$ follow up Email, the system may send 2 more Emails every week for 2 weeks. If a response is received from any of the emails, the process goes back to the Response received step, otherwise, if there is still no response received after the 3 Emails, the system may send an alert to a Follow Up Coordinator, who may call the Specialist to find out more details.

If the Follow Up Coordinator learns from the Patient that the Patient has already completed the Appointment, the Referral status may be changed to "3—Exam Done", and the Follow Up Coordinator may send the system generated bar code to the Specialist, who may then send the Report with bar code attached. Afterwards, the system may send the received Report with bar code to the PCP Office automatically, with Referral status changed to "4—Complete with Report". Similarly, if the Patient has NOT completed the Appointment, the (a)-(d) scenarios described above may be applied.

The bar code may be generated by the system, using the "Universal Product Code" format and in AVERY 8366™ size.

Inputs for the Follow Up Referral Appointment Process may include scheduled Referral Appointment information and response information received via Email from a Specialist.

Outputs for a Follow Up Referral Appointment Process may include updated Referral records and notifications sent to Patient and PCP.

Most of the activities in this process may be automatically done by the system, and the Role included may be the Follow Up Coordinator, whose responsibility may be to contact the Specialist to find out more details about the Appointment when an alert has been received.

TABLE 5

System Rules Description

Follow up Email may be sent automatically with options/link for Specialist to respond with feedback.
Follow up Fax may be sent automatically for Specialist to fill in feedback and fax back.
Follow Up Coordinator may contact Specialist to find out more details when the auto Email receives no feedback.

TABLE 6

System Requirements Description

One week after the scheduled date, follow up Emails may be sent to Specialists asking the following questions with options/link to send the feedback back:
  Has Patient Completed the Appointment? - Yes or No
    If "Yes", go to the next question
    If "No", select from the following conditions:
      Patient has rescheduled Appointment -
      if selected, reschedule date needs to be entered
      Patient was No Show
      Patient cancelled Appointment
  Is the Report Ready? - Yes or No
Referral status may be updated based on answers received via a follow up link sent in the follow up Emails.
Reschedule date may be updated to the Referral, if received.
If Patient was No Show for the appointment, the Referral status may be updated to "5 - Patient Disregard" with sub-status as "No Show".
If Patient cancelled the appointment, the Referral status may be updated to "5 - Patient Disregard" with sub-status as "Cancellation".
Notifications may be sent to Patient and PCP if Patient was No Show or Cancelled the appointment.
If the 1$^{st}$ Email was not answered, 2 more emails may be sent every week after.

TABLE 6-continued

System Requirements Description

If 'Has Patient Completed the Appointment? = Yes' and 'Is Report Ready? = Yes', system may send (e.g., via email or fax) the generated unique bar code to Specialist, who may then attach the bar code to Report and send it back to System.
Report with bar code may be faxed back, and system may be able to read bar code and attach received Report to corresponding Referral record automatically.
After the Report is received from Specialist, the Referral status may be updated to "4 - Complete with Report" automatically. Unique bar code may be generated and attached to the report, and sent to
After the Report is received from Specialist, the Report without bar code attached may be faxed and/or emailed to the PCP office.
If Report is NOT received, Reminder notification may be automatically sent to Specialist one week after the $1^{st}$ follow up notification.
Alert may be sent to Follow Up Coordinator if no response received after 3 follow up Emails, or no report received after 1 reminder.

Figure 4:
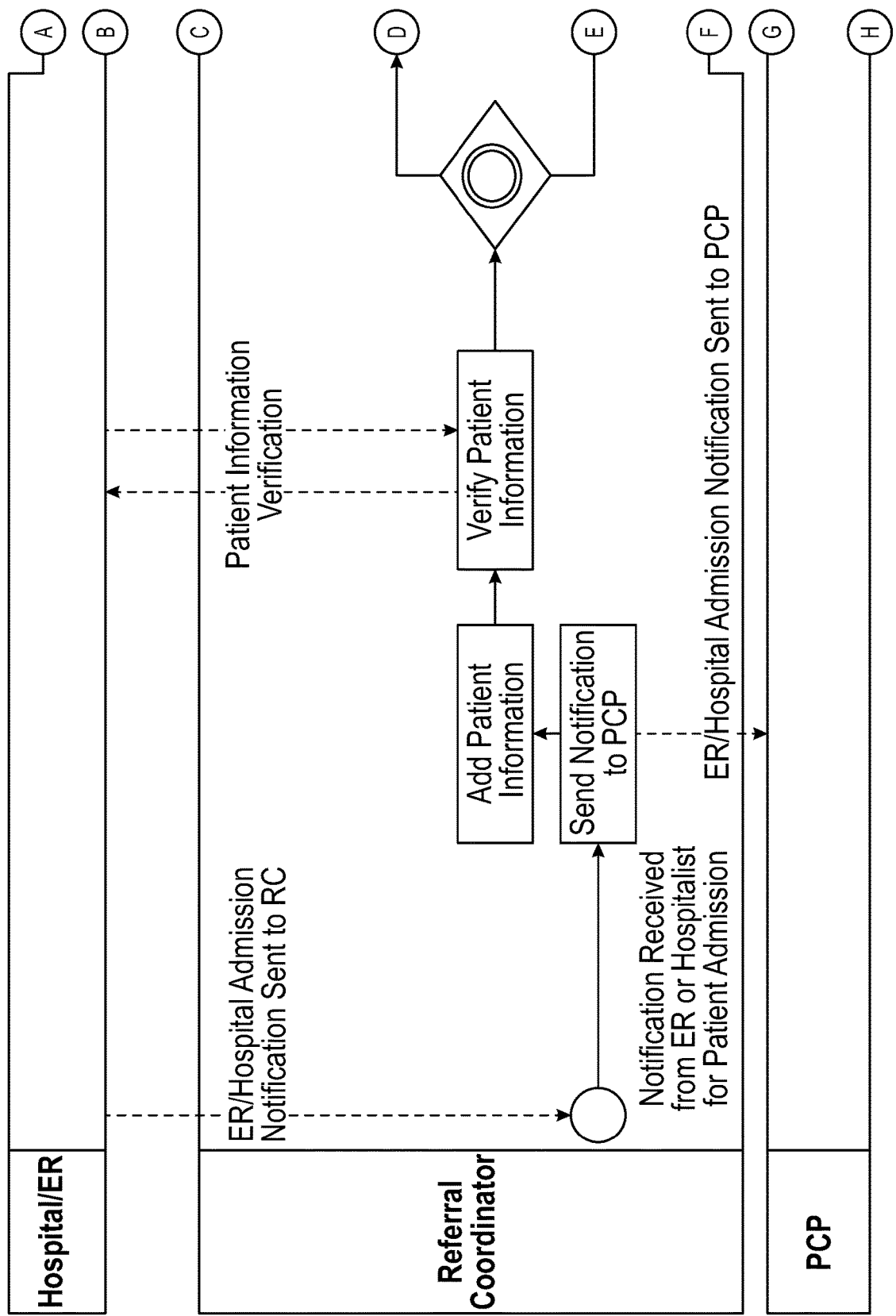
FIG. 4 is a workflow diagram depicting an ER and Hospital Admission Referral Process of an exemplary embodiment.
Figure 4:
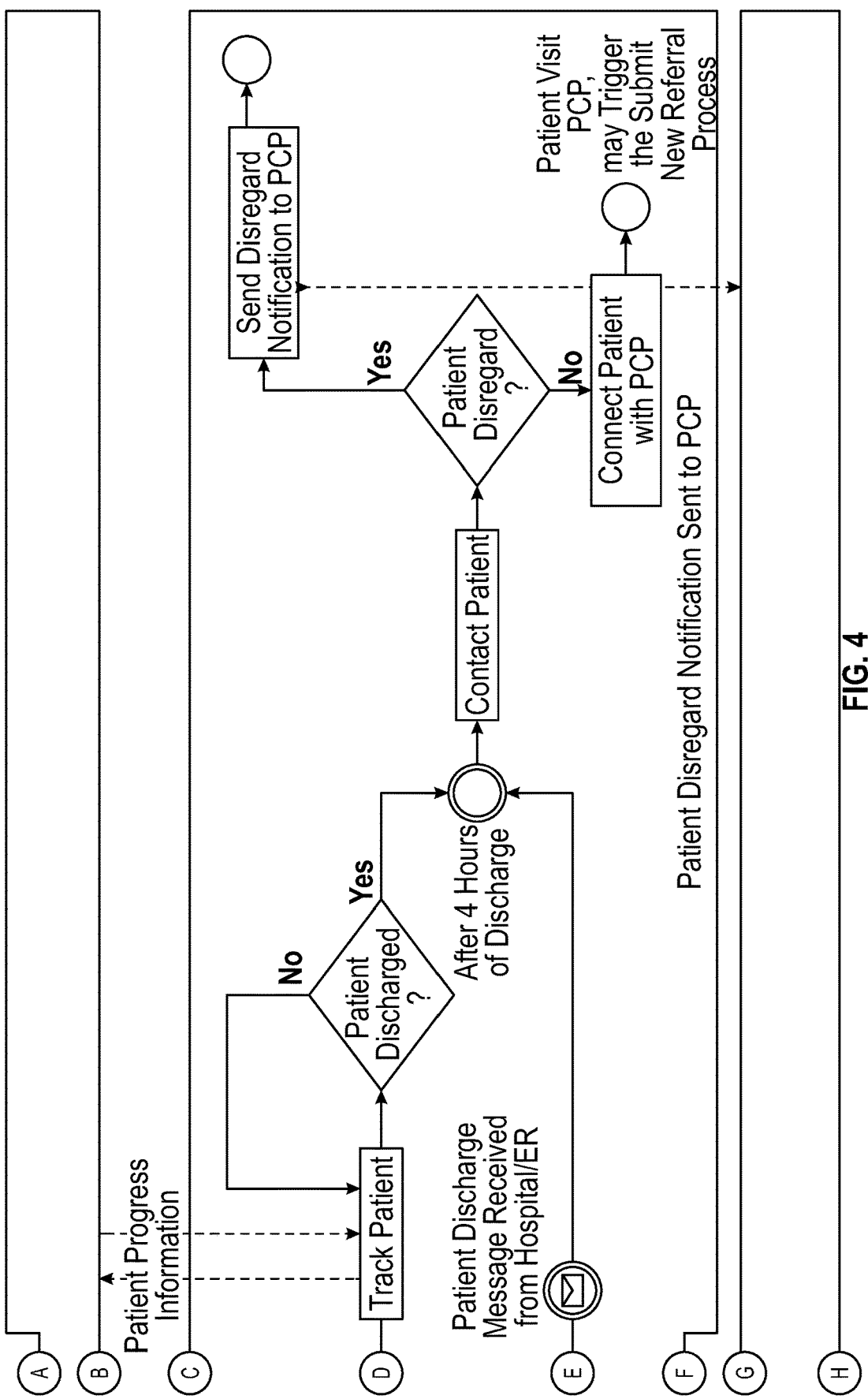

An ER and Hospital Admission Referral Process may be triggered when notifications received from a Hospital/ER for a Patient's admission. Referral Coordinators may then keep track of the Patient's progress and contact the Patient for Referral after discharge. See FIG. 4.

When the Patient arrives to an ER, staff may ask for his PCP's information, and notifications may be sent to the PCP and the system from a hospital secure email server to an associated secure email recipient (PCP and System) for this new admission. It's also possible that the Patient is admitted at ER and then transferred and admitted to a Hospital as a normal admission. When the Patient arrives at the Hospital as a normal admission, the Patient may be added to a Hospital list, and notifications may be sent to the System for this new admission.

An ER and Hospital Admission Referral Process may be triggered when notifications received from a Hospital/ER for a Patient's admission. A Referral Coordinator may then send notifications to the Patient's PCP and add the new admission record for the Patient if the Patient already exists in the system, or if a new Patient to the system, add the new Patient's profile with the new admission record.

The Referral Coordinator may also verify the Patient's information by logging into a secure hospital Citrix portal, as well as keep track of the Patient's progress and discharge status daily. When either discharge notification may be received or discharge status changed with daily check-in, the system may contact the Patient 48 hours after his discharge.

When contacting the Patient, the system may either connect the Patient with the PCP office for further scheduling, or send a Disregard notification to the PCP if the Patient disregards the referral.

Inputs for the ER and Hospital Admission Process may include:

Admission notifications from Hospital and/or ER

Verified patient information from Hospital

Patient progress information from Hospital and/or ER

Patient discharge notification from ER

Outputs for the ER and Hospital Admission Process may include notifications sent to PCPs.

A Role involved in this process may be the Referral Coordinator/system, whose responsibility may be to keep track of the Patient's discharge status and contact the Patient for referral.

TABLE 7

System Rules Description

When Patient is admitted to an ER, the ER may ask for his PCP information, and ER admission notifications may be sent to the PCP and System.
When Patient is admitted to a Hospital, the Hospital may add the Patient to a Hospital list of Patient Admission, and send to System.
When Patient is admitted to ER or Hospital, notifications may be sent to the Patient's PCP office automatically.
System staff may login to a Citrix portal to verify the Patients' information.
System staff may track the Patient's progress and discharge status by communicating with the Hospital.
48 hours after Patient's discharge, System may contact Patient.

TABLE 8

System Requirement Description

Notifications may be received from ER/Hospital for Patient Admission, with date/time captured.
System may send notifications to PCP office, through fax or email, when Patient Admission notification is received from ER/Hospital.
Patient Admission Record may be created and attached to Patient profile.
Patient information may be verified by logging into Citrix portal.
Patient discharge notification may be received.
Patient discharge date/time may be captured.
System may send notifications to PCP office (e.g., through fax or email) when Patient disregards System's follow up request.

SYSTEM DESCRIPTION AND FUNCTIONAL REQUIREMENTS
USER MANAGEMENT

Both Client users, including Primary Care Provider and Client Admin, and System Staff users may have direct access to the system. The following users may be created and granted with access to the system:

Client Side:

Healthcare System Admin User, who has access to all data within the network, including all the Hospitals; may be created by System Admin User.

Hospital Admin User, who has access to all data within the Hospital; may be created by System Admin User.

Primary Care Provider (PCP) User, who may be associated with or without Hospital(s), and have access to data of Patients under him, therefore submit the new Referral record; PCP may be able to self-register with temporary login provided by System:

I. System Admin User may create temporary Login (username and password) for PCP who uses the system.

II. PCP User logs in with the temporary credential and completes the registration information, including signing HIPAA and BAA agreements.

III. PCP completes the self-registration and obtains the valid credential for the system as an official user.

PCP Office Staff User, who preferably may only submit and check Referrals for PCPs in the same office; may be created by PCP User or System Admin User.

System Side:

Admin User, who has access to all system data and admin permissions

Referral Coordinator Manager, who has access to data of assigned Healthcare System and Hospital(s), and may generate reports for assigned network and coordinators that work underneath assigned network Referral Coordinator, who coordinates between Patient and Specialist, for appointment scheduling, referral tracking and follow ups, and has access to data of assigned Hospital Network and Hospital(s)

Follow Up Coordinator, who may be responsible for Referral follow ups, and have access to data of assigned Hospital Network and Hospital(s)

Users may be defined as people who interact with the system in various capacities (roles) to perform respective operations in the system.

Roles may be defined as different operations that may be required to interact with the system in various capacities to perform respective operations in the system. A user preferably may use the system with a defined role only.

There may be two types of user: Client User and System Staff User. For each user type, different User Roles may be defined and assigned.

For each User added in the system, a User Account and Login may be created, so that the User may be able to login to the system, access authorized data and functions, and manage his own account information.

TABLE 9

| Functional Requirement Description |
| --- |
| System may require User Type - Client User or Staff User, to be defined when creating new User. |
| System may require User Role to be defined for each User Type when creating new User: |
|   Client User Type: |
|     Healthcare System Admin |
|     Hospital Admin |
|     PCP |
|     PCP Office Staff |
|   Staff User Type: |
|     Staff Admin |
|     Referral Coordinator Manager |
|     Referral Coordinator |
|     Follow Up Coordinator |
| System may allow list of Users to be searchable, based on logged in User's access. For example, Healthcare System Admin User may search and view Users within the network, Hospital Admin User may search and view Users within the same Hospital, System Staff User may search and view all Users in the system. |
| System may allow User details to be viewed. |
| One Client User can only be associated with one Role. |
| One Staff User may be associated with more than one Role. |
| System may display different required information fields depending on different User Type and Role. For example, Healthcare System Admin User may be associated with Healthcare System, PCP Office Staff User may be associated with PCP Office location, etc. |
| System may allow authorized user to add/view/update Role. |
| A valid and unique Role name may be required. |
| Every Role may be associated with permission matrix. |
| Permission matrix may be pre-defined, consisting of process and actions. |
| System may allow permission matrix to be configurable as per requirement. |
| Permission matrix associated with Role may be unique. |
| Available Dashlets may be pre-defined for each Role. |
| System may allow Role to be activated and deactivated. |
| System may allow authorized user to search Roles. |
| When creating new User, System Admin needs to first select User Type (Client User, or Staff User) and User Role. |
| If User Type = Client User, only one Role can be assigned to the User; otherwise if User Type = Staff User, multiple Roles can be assigned to the User. |
| Fields to be filled to create new User may be different; depends on the entry of User Type and User Role. |
| When creating new User, System Admin may set up Username and Password. |
| If Email is provided, it can be checked to be used as Username, but not mandatory. |
| Email may be required for Staff User, but not for Client User. |
| If provided, Email address needs to be in valid format and unique. |
| If Email is provided, System may send verification email to User's provided email address, with Username and ask Password information, so that User can login and reset Password. |

TABLE 9-continued

| Functional Requirement Description |
| --- |
| For first time log in, User may be required to reset the Password. |
| Password needs to be validated against standard requirements, min characters, mixed case, mixed characters/numbers. |
| All authorized user may login to the system with valid credentials |
| System may allow user to login with Email or Username and Password. |
| System may record both successful and failed login attempts of User, with an audit log. |
| Account may be locked after three login failure attempts. |
| User may need to contact System Admin if account locked. |
| User may be able to click "Forgot Password", and system will ask user to enter Username: |
|   1) Valid Username/Email entered: |
|   a. Valid Email: system will send a Reset Password email to the valid registered Email |
|   b. Valid Username: system will ask user to provide an Email address to send the Reset Password email; and User can choose to enter an Email or contact the System Admin |
|   2) Invalid Username/Email entered: since the entered Username/Email is not valid, error message will be displayed; or user needs to contact the System Admin for password reset |
| Logged in user may only access data that may be authorized for that user, based on account settings (user type, user role, associated entities, etc.) |
| System may provide HIPAA secure logins with SSL certificate. |
| System may allow user to reset password after logging in. |
| By a user clicking the reset password link, system may send reset password link to user's email address. |
| The new password may not be the same as old password, and may also be validated against standard requirements. |
| User may be able to update own information after being logged in. |
| System may send verification emails to previous and new email addresses, if user choose to change email address. |
| New email address may be valid only after user verification, and old email address may be invalid for login. |
| System may automatically log Users out (time out) after [X] period of inactivity. |
| User may be able to click "Sign Out" to manually sign out. |
| System may record all the Sign In and Sign Out activities of User, including: |
|   User's IP address |
|   Sign In Time |
|   Sign Out Time |
|   Signed in duration |

A Healthcare System, including one or many Hospitals, may be considered as the System's client; so that each Healthcare system may have one record created in the system, with one or more Hospitals attached.

For each Healthcare System record, there may be Healthcare Admin User who has access to all the data within the network, including all the Hospitals attached. Under each Healthcare System, there may be one or multiple Hospitals, and for each Hospital, there may be a Hospital Admin User who has access to all the data within that Hospital. A PCP may be associated with one or multiple Hospitals.

One PCP may have multiple offices, and sometimes office staff submit Referrals on behalf of the PCP; so each PCP may be associated with one or multiple office locations. For each office, an Office Staff User may be created to only have access to Referrals under the same office.

TABLE 10

| Functional Requirements Description |
| --- |
| System may allow Healthcare System record to be created and saved. |
| System may allow Healthcare System Admin User to be created and assigned to Healthcare System. |
| Healthcare System Admin User may login to the system and have access to all data under the assigned network, including: |

TABLE 10-continued

Functional Requirements Description

Hospital records
PCPs accounts
  PCP Offices
  Patients information
Referral records
ER/Hospital Admission records
INN and OON lists
Report
Healthcare System Admin User may add/view/update Hospitals information under its network.
Healthcare System Admin User may add/view/update Referral records under its network.
Healthcare System Admin User may add/view/update the In-Network Specialist list.
Healthcare System Admin User may generate and view reports with all data under its network.
System may allow Hospital to be created and saved.
Healthcare System Admin User may add new Hospital Admin User to Hospitals under its network.
System may allow Hospital Admin User to be created and assigned to Hospital.
Hospital Admin User may login and only have access to data under the assigned Hospital, including:
  PCPs accounts
    PCP Offices
    Patients information
  Referral records
  ER/Hospital Admission records
  Report
Hospital Admin User may add/view/update Referral records under the assigned Hospital(s).
Hospital Admin User may generate and view reports with all data under the assigned Hospital(s).
System may allow authorized System user to create temporary login (temporary username and password) for PCP, who may be maying to sign up and use the system.
The PCP temporary login may already be associated with Healthcare System/Hospital, or without as individual PCP.
System may allow a PCP to be associated with one or more Healthcare Systems/Hospitals, or none (as an individual PCP).
The temporary login may only be valid within 48 hours.
System may allow PCP to login with temporary login received from System.
System may require PCP to change the temporary username and password after logged in.
System may allow PCP to sign HIPAA and BAA agreements, during registration.
System may require PCP to complete all the required fields to complete the registration.
System may allow PCP to login with new credential, after registration.
Patient profiles may be added under PCP, and only associated PCP may add new Patient information underneath him.
PCP User may login and have access to data of Patients associated with.
PCP User may submit new Referral for Patient associated with.
PCP User may generate and view report for Referrals submitted by himself.
System may allow new Location to be added.
System may allow PCP User be associated with one or multiple Office Locations.
System may allow PCP User to create PCP Office Staff User, for associated Office Locations.
System may allow Office Staff User be created and assigned to Office Location.
Office Staff User may only be able to submit new Referral on behalf of PCP within the same Office Location.

On the System side, an Admin User may have access to all data in the system and be granted with all permissions, including user account management, referral management, ER/Hospital admission management, case management and reporting.

Besides Admin User, a Referral Coordinator Manager, Referral Coordinator and Follow Up Coordinator User may be created and assigned to client accounts—Healthcare System records and/or Hospital records; so that they only have access to data of assigned accounts.

TABLE 11

Functional Requirements Description

Staff Admin User may be a super user who may be granted with all system permissions.
Staff Admin User may access all data in the system, including data from all Healthcare Systems.
Staff Admin User may add/view/update new User to the system.
Staff Admin User may add/view/update Healthcare System record in the system.
Staff Admin User may add/view/update Hospital record in the system.
Staff Admin User may add/view/update PCP record in the system.
Staff Admin User may add/view/update Patient record in the system.
Staff Admin User may add/view/update Specialty in the system.
Staff Admin User may add/view/update Specialist in the system.
Staff Admin User may add/view/update Referral in the system.
Staff Admin User may add/view/update ER/Hospital Admission record in the system.
Staff Admin User may generate and view report with all system data.
Referral Coordinator Manager, Referral Coordinator and Follow Up Coordinator may be assigned to Healthcare System and/or Hospital.
Referral Coordinator Manager, Referral Coordinator and Follow Up Coordinator may only have access to data of assigned Healthcare System/Hospital.
System may send notifications to assigned Referral Coordinator Manager when new Referral submitted for the Hospital.
Referral Coordinator may only assign new Referrals to Referral Coordinator assigned to the same Hospital.
System may send referral follow up alert to Follow Up Coordinator assigned to the same Hospital.

After being logged in, a user may be landed in (displayed) a Dashboard page, which may be customized by each individual user with available dashlets based on the user's role.

TABLE 12

Functional Requirements Description

System may land user on the Dashboard page, after user is logged in.
System may allow user to view assigned pre-defined dashlets as per their role.
System may allow user to configure their Dashboard, with the following information:
  Available Pre-defined Dashlets
  Shown Dashlets
  Hidden Dashlets
  Left Column Dashlets
  Right Column Dashlets
System may allow user to configure the Dashboard page by clicking Show or Hide assigned dashlets.
System may allow user to configure the Dashboard page by drag and drop dashlets in "Left Column" and "Right Column" to add them to their dashboard display.
User may save their dashlet configuration and the same may be visible to them on their login.

A Healthcare System may be a network or group of hospitals that work together to coordinate and deliver a broad spectrum of services to their community. Under one Healthcare System, there may be one or many Hospitals associated.

For each Healthcare System, there may be one or more Healthcare System Admin User(s), who each have access to all the Hospitals under the system and may generate reports with those data.

Each Healthcare System may have its own In- and Out-of- (leakage) Network list, and PCPs and Specialists may be associated with Healthcare System(s).

TABLE 13

Functional Requirements Description

System may allow Healthcare System to be created and saved.
System may allow authorized user to search for Hospitals. For example, Healthcare System Admin User may be able to search for Hospitals within the same network, System Staff User may be able to search for all the Hospitals.
System may allow Healthcare System Admin User to be created and assigned to Healthcare System.
Healthcare System Admin User may have access to all data under the assigned network.
Healthcare System Admin User may generate reports with all data under the assigned network.
System may allow Hospital to be created and saved.
System may allow Hospital Admin User to be created and assigned to Hospital.
Hospital Admin User may have access to all data under the assigned Hospital.
Hospital Admin User may generate reports with all data under the assigned Hospital.
System may allow one or multiple Hospital(s) be associated with one Healthcare System.
System may allow System users, including Referral Coordinator Manager, Referral Coordinator and Follow Up Coordinator, to be assigned to Healthcare System.
System may allow System users, including Referral Coordinator Manager, Referral Coordinator and Follow Up Coordinator, to be assigned to Hospital.
System may allow PCP to be associated with Healthcare System and/or Hospital.
System may allow Specialist to be associated with Healthcare System and/or Hospital.
In- and Out-of (Leakage) Network list may be attached to Healthcare System.

A primary care provider (PCP) may be a health care practitioner who sees people that have common medical problems. Patients need to visit their PCP first, then may be referred to Specialists. A PCP may need to sign up with the System in order to use the Referral platform, by signing BAA and HIPAA agreements. Once the PCP has registered with the System, a unique login may be created for that PCP.

A PCP may be associated with a Healthcare System and/or a Hospital, or without any Healthcare System/Hospital (as an Individual PCP). For most cases, one PCP may be associated with one Hospital, but the system is sufficiently flexible to allow multiple Hospitals to be associated with one PCP.

Each PCP may have its own list of Patients, only for whom the PCP may have access to view/update patient information and submit Referrals.

Each PCP may have one or many different offices, each of which may be associated with that PCP. For each PCP office, there may be at least one PCP Office Staff User who may submit Referrals on behalf of that PCP.

TABLE 14

Functional Requirement Description

System may allow a PCP account to be created and saved.
System may allow authorized users to search for PCPs. For example, a Healthcare System Admin User may search for PCPs within the same network, a Hospital Admin User may search for PCPs within the same Hospital, and a System Admin User may search for all PCPs in the system.
System may allow a PCP to be only associated with one Hospital (at a specific address), and Healthcare System will be recognized based on selection of Hospital.

TABLE 14-continued

Functional Requirement Description

System may allow a PCP to be created without associating it with any Healthcare System/Hospital, as an Individual PCP.
System may allow multiple PCP Office Locations to be associated with PCP.
For each PCP Office, at least one PCP Office Staff may be defined.
For each PCP Office, Communication Preference may be defined.
For each PCP Office, Office Hours may be defined.
System may allow a PCP Office Staff User to be created and associated with Office location.
A PCP Office Staff User may only submit a Referral on behalf of a PCP within the same Location.
PCP may only submit a Referral for its own Patient.
PCP may be able to generate and view a report with data of its own Patient.
System may allow an authorized System user to create a temporary login (temporary username and password) for PCP using the system.
The PCP temporary login may already be associated with a Healthcare System/Hospital, or an individual PCP.
The temporary login may only be valid within 24 hours.
System may allow a PCP to login with a temporary login received from System.
System may require PCP to change the temporary username and password after being logged in.
System may allow PCP to sign HIPAA and BAA agreements, during registration.
System may allow PCP office locations to be added, during registration.
System may enforce PCP to fill all the required fields to complete the registration.
System may allow PCP to login with new credential, after registration.
Authorized Staff user may be able to review and approve PCP.
Only approved PCP may be able to log into the system.
Patient profiles may be added under PCP, and only associated PCP may be able to add new Patient information underneath him.

TABLE 15

Functional Requirement Description - Patient Management

System may allow a Patient profile to be created and saved.
Patient profile may only be added by PCP, but may be updated by System staff Users.
System may allow Patient profile to be updated and saved.
System may allow authorized user to search for Patients. For example, Healthcare System Admin User may search for Patients within the same network, Hospital Admin User may search for Patients within the same Hospital, PCP User may search for Patients associated with him, System Staff User may search for all Patients in the system.
Patient profile may be attached to one PCP.
Patient's preferred language may be added and updated.
Patient's insurance information, including insurance provider, insurance plan, etc. may be added and updated.
Patient's billing information may be defined: whether self-pay, or paid by insurance.
System may attach Referral and ER/Hospital Admission records to Patient profile.
For each Patient profile, system may allow the history of Referral records to be viewed.
For each Patient profile, system may allow the history of ER/Hospital Admission records to be viewed.

TABLE 16

Functional Requirement Description - Specialty Management

System may allow the list of Specialty to be pre-defined.
System may allow new Specialty to be added.
System may allow Specialty list to be updated.
System may allow authorized user to search for Specialty, such as System Staff Admin User.
System may allow Specialty to be selected from the pre-defined list when adding new Referral.
System may allow Specialty to be associated with Specialist.

TABLE 16-continued

Functional Requirement Description - Specialty Management

System may display Specialists who may be associated with selected Specialty, when adding new Referral.

TABLE 17

Functional Requirement Description - Specialist Management

System may allow a Specialist profile to be added and saved.
System may allow a Specialist profile to be updated and saved.
System may allow a Specialist profile to be added with Specialties.
System may allow Specialist to be associated with one or more than one Hospital.
System may allow Insurance and Insurance Plan information to be defined for each Specialist.
System may allow authorized user (System Admin User) to add or remove Specialists to or from INN list and ONN (Leakage) list, for selected Hospital.
System may allow Specialist profile to be associated with multiple Office Locations.
System may allow authorized user to search for Specialists.
System may allow Referral to be attached to Specialist profile.
System may allow authorized user to view the history of Referral records of selected Specialist.

TABLE 18

Functional Requirement Description - Location Management

System may allow Location to be added and saved.
System may allow Location to be updated and saved.
Operation hours may be defined for each Location.
System may allow authorized user to search for Locations.
System may allow Location to be associated with PCP and Specialist.
System may allow one Location to be associated with multiple PCPs and/or Specialists.
If the Location may be associated with PCP, system may identify it as PCP Office and allow PCP Office Staff User to be associated.
For each Location, a Primary Contact needs to be defined, so that all communications may be sent to this Contact.
System may allow communication preference to be set up for each Location.

TABLE 19

Functional Requirement Description - Insurance Management

System may allow an Insurance Company record to be added and saved.
System may allow an Insurance Company record to be updated and saved.
System may allow an authorized user to search for Insurance Company records.
System may allow added Insurance Company records to be selected when adding new Referral.
System may allow Insurance Plan to be added under Insurance Company.
System may allow Insurance Plan to be updated and saved.
System may allow authorized user to search for Insurance Plan records.
System may allow added Insurance Plan to be selected when adding new Referral.
System may identify whether the Insurance Plan requires authorization for Referral Appointment scheduling.

When a Patient visits his Primary Care Provider (PCP), and the PCP decides that a Specialist needs to be referred for this Patient—and this may be when a new Referral request may be submitted into the system.

When the Referral record is in the System, a System staff user may then schedule the appointment and keep track of the Referral.

TABLE 20

Functional Requirement Description - Referral Management

System may allow a PCP to submit a new Referral for a Patient associated with that PCP.
System may allow a PCP Office Staff User to submit a new Referral on behalf of PCP within the same office, by selecting the PCP first.
System may allow Patient to be selected if the Patient already has a profile in the system.
System may allow new Patient profile and information to be added and saved, if the Patient is new.
System may allow Patient information to be updated and saved, while adding a new Referral.
System may pre-populate a Patient's insurance company and details if already in the Patient's profile.
System may allow a Patient insurance company to be selected and information to be added and saved, while adding new Referral.
System may allow Patient insurance information to be updated and saved, while adding new Referral.
System may allow Patient billing information to be added and saved, while adding new Referral.
System may allow Patient billing information to be updated and saved, while adding new Referral.
System may allow Patient's preferred language to be defined, while adding new Referral, and the default language may be English.
System may allow Patient's Diagnosis Code(s) to be defined.
System may allow Specialty to be selected from the pre-defined list.
System may list Specialists based on the selection of insurance company and Specialty - only Specialists within the insurance's network and associated with selected Specialty may be listed.
System may allow new Specialist to be added, while adding new Referral.
System may ask to select one of the Specialist's Location, if multiple Locations may be associated.
System may ask to select the Referral Type - Normal or STAT.
System may allow Special Instructions/Patient history to be added for the Referral.
System may allow Notes to be added for the Referral.
System may allow the Referral request to be signed and submitted.
Once the Referral is submitted:
  For STAT Referrals, system may send notifications to assigned Referral Coordinator Manager right away.
  For Normal Referrals, system may send notifications to assigned Referral Coordinator Manager by end of day, with a count and summary of Normal Referrals.
System may allow multiple Referrals to be submitted for the same Patient, all at once.
System may save the Referral, but not yet submit.
System may filter Referrals by Referral Status and sub status.
Once the Referral is submitted, the Referral status may be "1 - New".
System May allow Referral Coordinator Manager to assign the "New" Referral to Referral Coordinator associated with the same Healthcare System/Hospital.
System may allow Referrals to be assigned individually or in bulk.
Once the Referral is assigned, system may send notifications to an assigned Referral Coordinator.
Once the Referral is assigned to a Referral Coordinator, the Referral status may be updated to "1 - New" with sub status as "Assigned".
If the $1^{st}$ call Referral Coordinator made to the Patient was not answered, system may send Reminder for $2^{nd}$ call in 2 days.
Once the Referral is be scheduled with appointment date, the Referral status may be updated to "2 - Scheduled" automatically.
System may send notifications to both Patient and Specialist when the appointment is scheduled.
If the Patient's Insurance does NOT require Authorization, once the Referral is scheduled it may also be automatically confirmed, with Referral status updated as "2 - Scheduled" and sub status as "Confirmed".
If the Patient's Insurance requires Authorization, once the Referral is scheduled, system may ask for Insurance Authorization.
System may allow insurance authorization to be attached to the Referral.
If the Patient's Insurance requires Authorization, and the Insurance Authorization is obtained, the Referral status may be updated as "2 - Scheduled" and sub status as "Confirmed" automatically.
System may send notifications to both Patient and Specialist when the appointment is confirmed.
Once the Referral is updated to status "2 - Scheduled", the full Referral script may be emailed and/or faxed to Specialist.
Patient may add the schedule date to Calendar when receiving the notification.
System may send Reminder to Patient [X] days (configurable) before the scheduled date.

TABLE 20-continued

Functional Requirement Description - Referral Management

System may allow Referral status to be changed to "5 - Patient Disregard".
System may allow Referral status to be changed to "6 - Unable to Contact".
For the Referrals with status changed to "5 - Patient Disregard" and "6 - Unable to Contact", system may send daily report to the PCP Office.
System may send follow up Email to Specialist, one week after the Appointment date automatically.
The follow up Email may include a link allowing a Specialist to select and
respond with answers to the following questions:
    I. Has Patient Completed the Appointment? - Yes or No
      i. If "Yes", goes to the II question
      ii. If "No", select from the following conditions:
        a. Patient has rescheduled Appointment - if selected, reschedule date needs to be entered
        b. Patient was No Show
        c. Patient cancelled Appointment
    II. Is the Report Ready? - Yes or No
System may read the answers sent back via the follow up link and update Referral automatically.
System may read the reschedule date sent back by the Specialist and update the Referral with the new date.
System may log all the Referral schedule history, including appointment date/time and change date/time.
If NO response received one week from the $1^{st}$ follow up Email, system may send $2^{nd}$ follow up Email in one week.
If NO response received one week from the $2^{nd}$ follow up Email, system may send 3rd follow up Email in one week.
If NO response received after 3 follow up Email sent, system may send Alert to Follow Up Coordinator(s) that are assigned to the same Healthcare System/Hospital, after three weeks since $1^{st}$ follow up Email.
System may flag the Referral as "Follow Up" needed.
System may allow Follow Up Coordinator to assign Referral to itself.
System may display "Follow Up" Referrals by Specialist Office Location, so that the Follow Up Coordinator may follow up multiple Referrals with the same Location within one call.
Once the Referral receives feedback as "Patient has completed the Appointment" but Report may be still NOT ready, the Referral status may be updated to "3 - Exam Done" automatically.
Once the Referral receives feedback as "Patient has completed the Appointment" but Report may be still NOT received after one week, system may send Reminder to Specialist asking for Report.
If after one week since the Report Reminder sent, the Report may be still NOT received, system may send Alert to Follow Up Coordinator(s) that assigned to the same Healthcare System/Hospital.
System may send follow up Alert to all Follow Up Coordinators assigned to the same Healthcare System/Hospital with the Referral, and one Follow Up Coordinator may assign itself to the Referral.
System may log all Referral assignment history.
Once the Referral receives feedback as "Patient has completed the Appointment" and "Report may be Ready", the Referral status may be updated to "4 - Complete with Report" automatically.
Once system has received "Yes" for "Is the Report Ready?", system may send the generated unique bar code to the Specialist, who may then attach it to the Report and send the Report to System.
System may also allow authorized user (Follow Up Coordinator) to click and generate the unique bar code for every Referral, and send it to Specialist who may then attach it to the Report.
Once the Report is received with bar code attached, system may send (fax and/or email) the Report to PCP Office and updated to "4 - Complete with Report" automatically.
System may also save the Report with bar code and attach it to the Referral in the system, so that it may be accessed by an authorized user.
System may be able to generate bar code with the "Universal Product Code" format and in AVERY 8366TM size.
Once the Referral receives feedback as "Patient has NOT completed the Appointment" and "No Show", the Referral status may be updated to "5 - Patient Disregard" with sub status as "No Show" automatically.
Once the Referral receives feedback as "Patient has NOT completed the Appointment" and "Cancellation", the Referral status may be updated to "5 - Patient Disregard" with sub status as "Cancellation" automatically.
Once the Referral status may be changed to "5 - Patient Disregard" with sub status as "No Show" or "Cancellation", system may send notifications to the Patient asking the Patient to call back and reschedule.
System may allow Referral status to be changed to "5 - Patient Disregard" with or without sub status.
System may allow Referral status to be changed to "6 - Unable to Contact".
System may allow Referral to be flagged as "Management Attention", which may send notifications to System Admin User and Referral Coordinator Manager automatically.
System may allow Notes to be added for Referral, with date/time captured.
System may allow Document to be attached to Referral.
Referral Coordinator Manager may assign Referral Coordinator to the Referral; and Follow Up Coordinator may be able to assign himself to the Referral.
Referral Coordinator and Follow Up Coordinator may be assigned and work on the same Referral.
System may allow Referrals to be searched by Healthcare System and Hospital.
System may allow Referrals to be searched by PCP and PCP Office.
System may allow Referrals to be searched by Patient information, including Patient Last and First Name, Patient DOB and Patient Insurance provider.
System may allow Referrals to be searched by Specialty, Specialist and Specialist Office.
System may allow Referrals to be searched by submission date range.
System may allow Referrals to be searched by appointment schedule date range.
System may allow Referral search criteria to be saved by naming it.
System may allow saved Referral search criteria to be retrieved and edited.

ER/Hospital Admission Management

When Patient has been admitted to an ER or Hospital, notifications may be sent to System. Therefore, an ER/Hospital Admission record may be added in the system for the Patient, and System staff may keep track of it.

TABLE 21

Functional Requirements Description

System may allow new ER/Hospital admission record to be added and saved.
System may allow new ER/Hospital admission record to be updated and saved.
System may allow authorized user to search for ER/Hospital admission record.
System may attach added ER/Hospital admission record to Patient profile.
System may send notifications to PCP Office when new ER/Hospital admission record added.
System may allow Patient Discharge date/time to be added.
System may send notifications to PCP Office when the Patient may be discharged.
System may allow Notes to be added for ER/Hospital admission record with date/time captured.
System may send notifications to PCP office, through fax or email, when Patient disregard System's follow up request.

Invoices may be generated based on number of Referrals and ER/Hospital Admission records created, applied with rates. Invoices may be generated for each Healthcare System account monthly.

TABLE 22

Functional Requirements Description

System may generate invoice for each Healthcare System account monthly.
Invoice may include total number of Referrals created, with rates applied, for each account.
Invoice may include total number of ER/Hospital Admission records created, with rates applied, for each account.
Invoice may be exported and printed.

Communication Management

TABLE 23

Functional Requirements Description

System may allow communication preferences to be set up for Patient, PCP, Specialist and Location - PCP Office and Specialist Office.
Communication preferences may include:
   Email, when selected Email address is required
   Text, when selected Cell Phone number is required
   Fax, when selected Fax number is required
   Mail, when selected Mailing address is required
System may send all communications, including notifications, reminders and alerts based on preferences and information provided.
System may report back if the Email failed to send.
System may report back if the Text failed to send.
System may report back if the Fax failed to send.

Report Management

There may be pre-defined reports that may be viewed by authorized users, who may also edit and save the new search criteria as a new report, as well as create new search criteria and generate reports periodically.

TABLE 24

Functional Requirements Description - Reports

System may allow user to view pre-defined reports, based on user roles.
System may allow user to change the search criteria for existing reports and save them as new ones.
System may allow user to create new search criteria to generate new reports and save them.
System may generate all the reports with real time data.
Report may be printed and exported as a "pdf" or "csv" or "excel" file.
End of Month Report - This may list a Referral count with PCP and Leakage information associated for each Specialty/Specialist end of month, for every Healthcare System. It may include:
   Referral Totals by PCP
   Referral Count by Status (both table and pie chart)
   Leakage Referral by Specialty
   In-/Out- Network Referral Count by Specialist and Specialty
   In-/Out-of- Network Referral Totals (both table and pie chart)
Mid-Month Report - This may list Referral count for PCP and totals, until the middle of each month, for every Healthcare System/Hospital. It may include:
   Referral Totals by PCP
   Referral Grant Total
Leakage Trend Report - This may list Referral leakage trend by Specialty and Location, for every Healthcare System. It may include:
   Leakage Count summary: display number of leakage by Year or Month for each Healthcare system (both table and column chart)
   Leakage Count by Specialty: display number of leakage based on Specialty by Year for each Healthcare system (both table and column chart)
   Leakage Count by Zip and Specialty: display number of leakage based on Zip code for each Specialty, by Year for each Healthcare System
   Leakage Cluster: display request cluster vs. leakage cluster on a map
Referral Density Report - This report may visualize the referral density based on criteria of PCP referrals to any Specialist, which may show where the referrals may be coming from and where the referrals may be going with numbers, on map. The Referral Density Report also may identify distance from the PCP to the Specialists, in miles. Thus, the hospital or healthcare system will be able to identify areas of need based on the number of referrals and distances patients are required to travel to place specialists in closer proximity to the PCP as required. This information may be obtained by reviewing the density report, the number of referrals, the distance of the patient's travel, and the specialist identified.

TABLE 24-continued

Functional Requirements Description - Reports

Healthcare System Summary Report - This may list Referral totals for each Healthcare System, for selected data range, so that System Admin may have an overview of all the systems.
New Referral Report - This may list all new Referrals that are submitted in the system but have not been taken care of.
Referral Assignment Report - This may list Referral count by assigned Referral Coordinator, including total number of Referrals assigned, number of Referrals scheduled, number of Referrals with status changed, number of Notes added for assigned Referrals, for each RC.
Daily Referral Submission Report - This may list Referrals submitted for the day, and may be sent to the Referral Coordinator Manager at end of the day.
Report Status Report - This may list Referrals based on status, including communication status, for selected Date Range, by Specialty; and System Admin User may also view it by Healthcare System.

TECHNICAL DESCRIPTION

The purpose of this Technical Description is to describe the technical design of the exemplary embodiments of the system and of exemplary system implementation. This description describes the modules of the system, and includes architecture and class diagrams, along with DB tables.

The description details functionality provided by each component or group of components of exemplary embodiments and shows how the various components interact.

An exemplary embodiment may comprise a website may be built using HTML 5 with JQuery1.1x. Data may be pulled from the SQL Database server using the Web API Controller. The Service Layer may be built using .NET C#. For all data-related needs, the Restful Service may be called, which in turn may fetch the data from the SQL Server and send the data back to the website.

An exemplary technical stack utilized for this system comprises the following five languages/APIs:
1. Front End development over HTML 5.0
2. Bootstrap (CSS)
3. JQuery 1.1x based Data binding/validation
4. .Net C# Based RESTful APIs
5. MS SQL Server 2014

Figure 5:
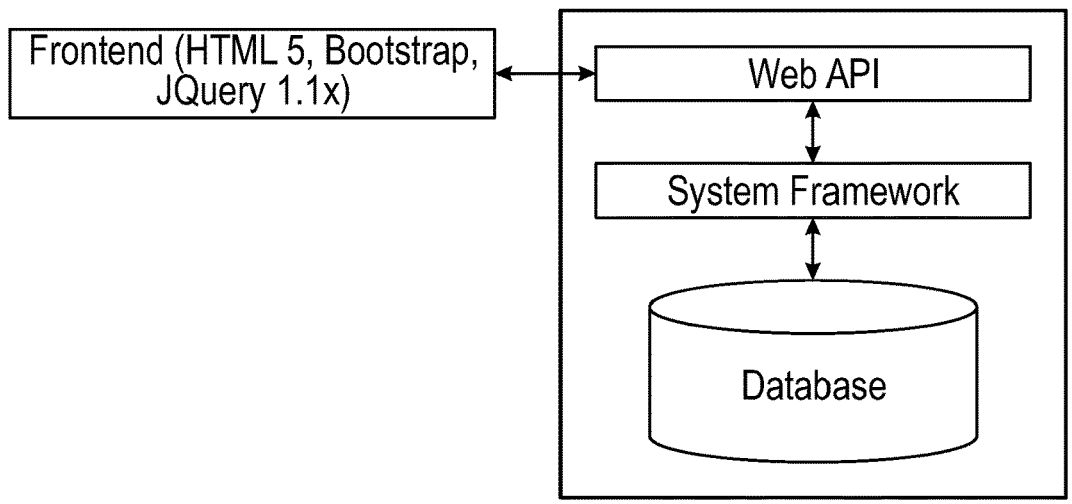
FIG. 5 depicts technical architecture of an exemplary embodiment.

Exemplary technical architecture is depicted in FIG. 5:

The system may be deployed on Cloud/web servers and may work in part as a web application. Other components such as Database and Services may also be deployed on secure (SSL) cloud/web servers. To use the system, a user may be within the domain network and may have appropriate credentials to login and perform certain operations.

Figure 6:
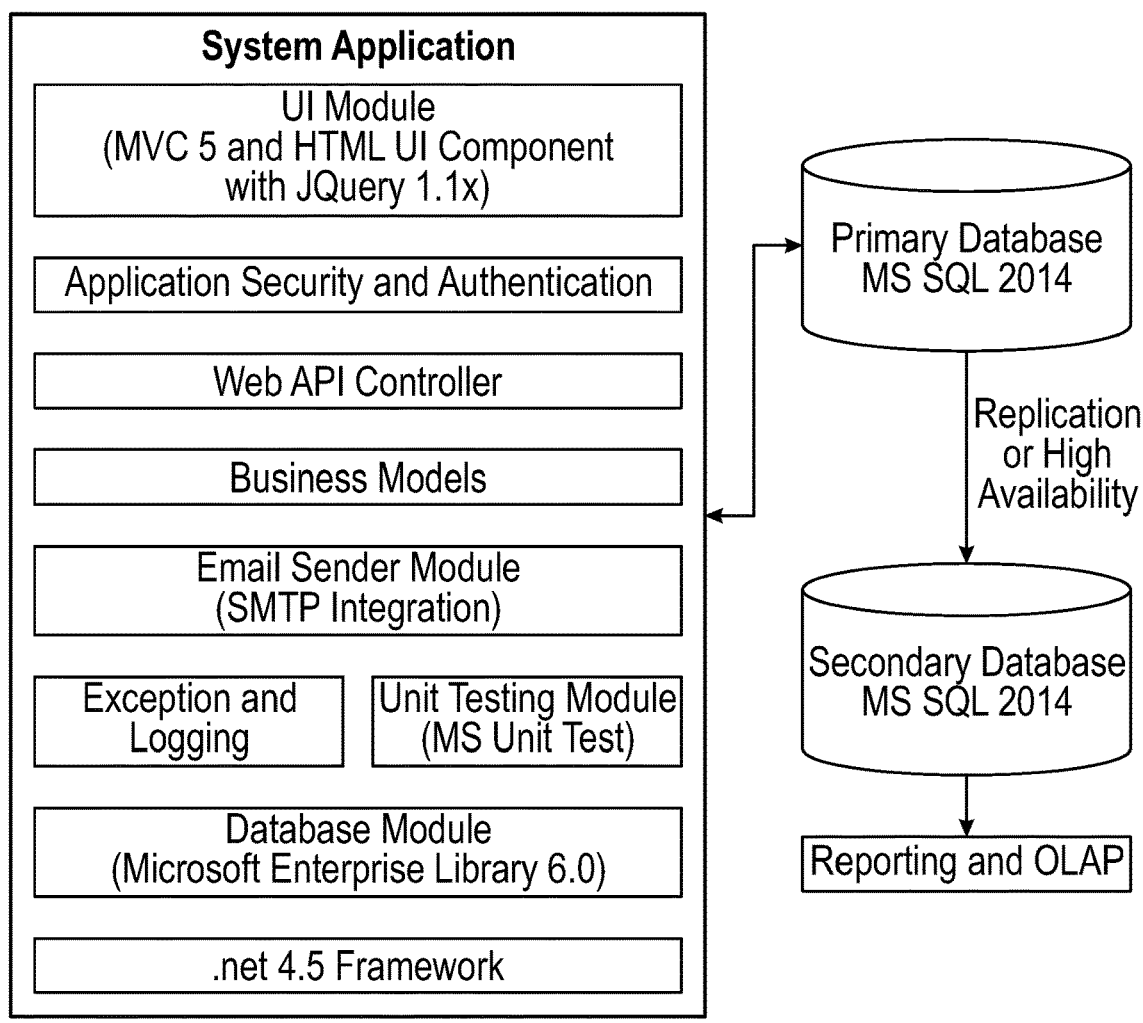
FIG. 6 is a logical and physical design diagram of an exemplary embodiment.

Logical and Physical High Level Design Diagram—FIG. 6

UI Module: Presentation layer which may be implemented with MVC 5 framework and HTML UI components.

Authentication: Login and Authentication may be done through System database and password may be encrypted through MD5 Hash.

Web API: Web API exposes restful end points. Depending upon the payload, it executes the corresponding system process and send out back to the client in JSON over HTTP.

Email Module: Mailing engine to send emails for forgot password, reset request, unlock user request etc.

Unit Testing Module: Unit tests may be written on a MS Unit testing framework.

Exception Logging: Class library for exception handling and logging to the database and sending notification to admin by email as well.

Database Layer: Data module uses Microsoft Enterprise Library 6.0 to interact with SQL Server 2014. Stored procedure and user defined function may interact to data layer.

Figure 7:
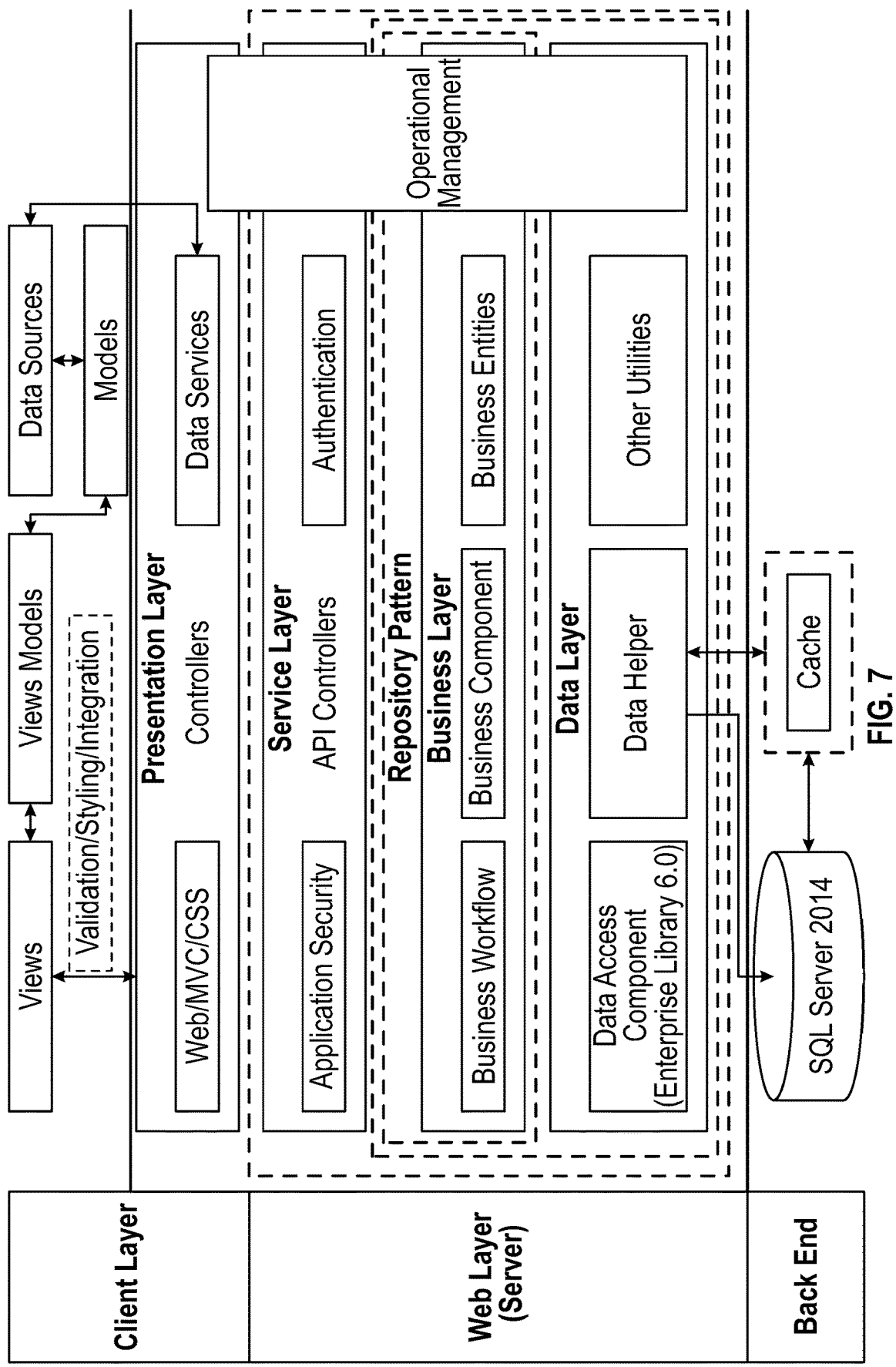
FIG. 7 is a system physical and logical design diagram of an exemplary embodiment.
Figure 8:
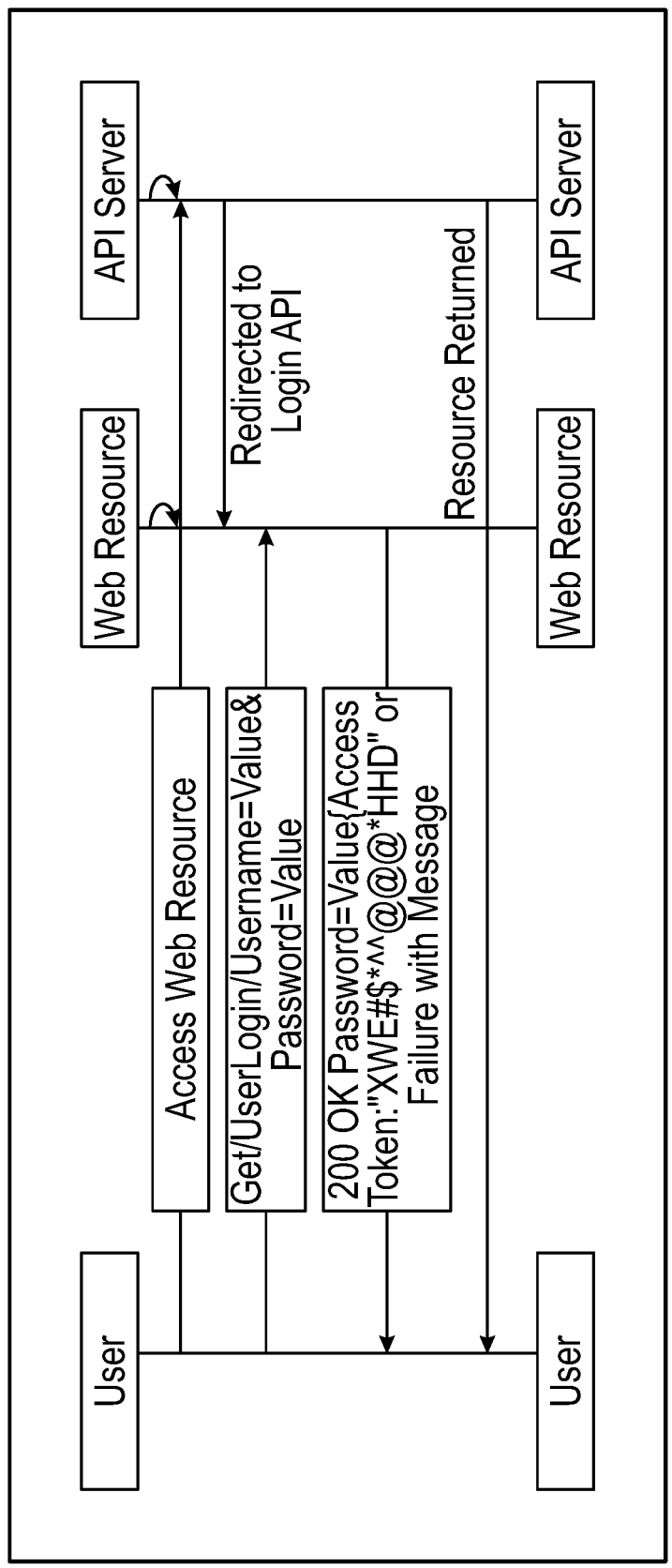
FIG. 8 is a diagram depicting an Authentication Process of an exemplary embodiment.

An exemplary System Physical and Logical High Level design diagram (FIG. 7) explains various components and their interactions in context of the system. The system may comprise a number of basic layers:

1. Backend
2. Web Layer (server)
3. Client Layer

Backend: includes the database (SQL Server 2014) of the system along with server side caching. Data Layer may consume the data provided by Backend Layer. Database interactions happen in the system through the help of the Repository System. All the repositories in the system may be derived from a Repository Interface. All other components of the system may use the repository interfaces to do any sort of data manipulation.

Web Layer (Server): may comprise the following layers:

Data Layer: This layer provides access to data hosted within the boundaries of the system. The data layer exposes generic interfaces that the components in the system layer may consume. It consists of Data Access Component (Enterprise Library 6.0), Data Helper and Other Utilities.

System layer: This layer implements the core functionality of the system, and encapsulates the relevant system logic. It consists of components, workflow and entities.

Presentation layer: This layer contains the user oriented functionality responsible for managing user interaction with the system, and comprises components that provide a common bridge into the core system logic encapsulated in the system layer.

In addition, Security and Operational Management may be provided on all the layers. Security includes Permissions, membership, xss attack, etc. Operational Management includes Logging information, Configuration, tracing, caching, etc.

Client Layer:

Client may access the web layer through Internet. This layer may be tightly coupled with view, model, and view models. Validations may be placed through JQuery.

Exemplary Security Features

1. Secure Login: Password may be saved an encrypted form in System database.

2. Access control and Authentication: Users may be restricted within the boundary of their role and permissions to access the component of the application. Each user has to be associated with some role and certain privileges of that role may be applicable on that user.

3. Brute force attack: Application blocked in case of more than 3 consecutive wrong password try to avoid brute force attack or automatic script login attack.

4. SQL injection: it's a common attack where attacker may append some sql script element with input to expose the internals of the application or damage the data. We verify every freeform input from the user.

5. Server side authentication and authorization: Even if attacker changes the UI elements or URL injection (appending the URL with id) to gain access the restricted information, still application do authorization of the request on server side and only grant access if user has right to access some resource.

6. Cross Site Scripting: The success of this attack requires the victim to execute a malicious URL which may be crafted in such a manner to appear to be legitimate at first look. When visiting such a crafted URL, an attacker may effectively execute something malicious in the victim's browser. Some malicious Javascript, for example, may be run in the context of the web site which possesses the XSS bug. Along with .NET framework's inbuilt functionality to validate the incoming Request and malformed URL, we have implemented a proper validation process of the input and anti-forgery token.

Users must be authenticated. Then a token gets generated by the system. All the subsequent calls may be verified by matching the Authentication Token, failing which the request gets terminated, with the attempting user being shown an appropriate message.

Platform Support

The website aspect may run on popular browsers available in the market, such as:

TABLE 25:

| Browser/Platforms |
| --- |
| Internet Explorer v-10 or higher /Chrome v-54 or higher /Firefox v-50 or higher /Safari v-5.1 or higher |
| All different mobile devices including IPhone, Samsung, LG and other models using the iOS, Android and Windows platforms |

APPENDIX

TABLE 26

| Dashboard - Dashlet Examples | | | |
| --- | --- | --- | --- |
| Dashlet Name | Type | User Role | Description |
| Healthcare System Referral Summary | Table | Healthcare System Admin | Display "Number of Referrals" categorized by Hospital, for selected date range - system may display data for current month by default, including:<br>Hospital Name<br>Total of Referrals<br>In-Network Referrals #<br>Leakage Referrals # |
| Leakage by Specialty/Specialist | Table | Healthcare System Admin | Display "Number of In-Network Referrals" and "Number of Leakage Referrals" by Specialty and Specialist, for selected date range - system may display data for current month by default, which also allows user to select All or One Hospital from the network; for each Specialty, Total In- and Out- Network Referrals # may first be displayed, then for each Specialist, |

TABLE 26-continued

Dashboard - Dashlet Examples

| Dashlet Name | Type | User Role | Description |
|---|---|---|---|
| | | | including:<br>　Specialty Name<br>　Specialist Last, First Name<br>　In-Network Referrals #<br>　Specialty Name<br>　Specialist Last, First Name<br>　Leakage Referrals #<br>* Clicking "More. . ." may redirect user to the Report - Leakage by Specialty/; Specialist Report page, with more details displayed. |
| Leakage Trend Summary | Column Chart | Healthcare System Admin | Display "Number of Leakage Referrals" by Year or Month, for selected Year/Month range in a column chart format for this Healthcare System, which also allows user to select All or One Specialty from the list; system may display "Number of Leakage Referrals" by Month for current year for All Specialty in total. |
| Referral by PCP | Table | Healthcare System Admin | Display "Number of Referrals" by PCP associated with this Healthcare System, which also allows a user to select All or One Hospital from the list, for selected data range - system may display data for current month by default, including:<br>　PCP Name<br>　# of Referrals<br>* Clicking "More. . ." may redirect user to the Report - Referral by PCP Report page, with more details displayed. |
| Referral Status Summary | Table, Pie Chart | Healthcare System Admin | Display "Number of Referrals" by Referral Status for this Healthcare System, which also allows user to select All or One Hospital from the list, for selected date range - system may display data for current month by default, including:<br>　Referral Status<br>　# of Referrals<br>　Percentage<br>* Clicking "Chart" icon may display the data in a pie chart format<br>* User may be able to switch between Table and Chart display<br>* Clicking "More. . ." may redirect user to the Report - Referral Status Report page, with more details displayed. |
| Top 10 Referral Specialty | Table | Healthcare System Admin | Display top 10 Specialties that get referred within this Healthcare System, for selected date range, including:<br>　Specialty Name<br>　# of Referrals |
| New Referral | Table | Healthcare System Admin | Display new referrals for the Healthcare System, which also allows user to select All or One Hospital from the Hospital list within the network, including:<br>　Referral #<br>　PCP<br>　Patient<br>　Specialty<br>　Specialist<br>　In/Out Network<br>* Clicking "More. . ." may redirect user to the Report - New Referral Report page, with more details displayed. |
| Hospital Referral Summary | Table, Pie Chart | Hospital Admin | Display "Number of Referrals" for this Hospital, for selected date range - system may display data for current month by default, including:<br>　Total of Referrals<br>　In-Network Referrals #<br>　Leakage Referrals #<br>* The data may also be displayed in a pie chart format, with In-Network and Leakage Referrals Percentage |
| Leakage by Specialty/Specialist | Table | Hospital Admin | Display "Number of In-Network Referrals" and "Number of Leakage Referrals" by Specialty and Specialist, for selected date range - system |

TABLE 26-continued

Dashboard - Dashlet Examples

| Dashlet Name | Type | User Role | Description |
|---|---|---|---|
| | | | may display data for current month by default; for each Specialty, Total In- and Out- Network Referrals # may first be displayed, then for each Specialist, including:<br>    Specialty Name<br>    Specialist Last, First Name<br>    In-Network Referrals #<br>    Specialty Name<br>    Specialist Last, First Name<br>    Leakage Referrals #<br>* Clicking "More. . ." may redirect user to the Report - Leakage by Specialty/; Specialist Report page, with more details displayed. |
| Leakage Trend Summary | Column Chart | Hospital Admin | Display "Number of Leakage Referrals" by Year or Month, for selected Year/Month range in a column chart format for this Hospital, which also allows user to select All or One Specialty from the list; system may display "Number of Leakage Referrals" by Month for current year for All Specialty in total. |
| Referral by PCP | Table | Hospital Admin | Display "Number of Referrals" by PCP associated with this Hospital, for selected data range - system may display data for current month by default, including:<br>    PCP Name<br>    # of Referrals<br>* Clicking "More. . ." may redirect user to the Report - Referral by PCP Report page, with more details displayed. |
| Referral Status Summary | Table, Pie Chart | Hospital Admin | Display "Number of Referrals" by Referral Status for this Hospital, for selected date range system may display data for current month by default, including:<br>    Referral Status<br>    # of Referrals<br>    Percentage<br>* Clicking "Chart" icon may display the data in a pie chart format<br>* User may be able to switch between Table and Chart display<br>* Clicking "More. . ." may redirect user to the Report - Referral Status Report page, with more details displayed. |
| Top 10 Referral Specialty | Table | Hospital Admin | Display top 10 Specialties that get referred for the Hospital, for selected date range, including:<br>    Specialty Name<br>    # of Referrals |
| New Referral | Table | Hospital Admin | Display new referrals for the Healthcare System - Hospital, including:<br>    Referral #<br>    PCP<br>    Patient<br>    Specialty<br>    Specialist<br>    In/Out Network<br>* Clicking "More. . ." may redirect user to the Report - New Referral Report page, with more details displayed. |
| New Referral | Table | PCP | Display new referrals submitted by this PCP, which also allows user to select All or One of PCP Office Location from the Locations list associated with the PCP, including:<br>    Referral #<br>    PCP Office<br>    Patient<br>    Specialty<br>    Specialist<br>    In/Out Network<br>* Clicking "More. . ." may redirect user to the Report - New Referral Report page, with more details displayed. |
| My Notifications | Table | PCP | Display notifications sent to this PCP, including:<br>    Notification Date<br>    Notification Description |

TABLE 26-continued

Dashboard - Dashlet Examples

| Dashlet Name | Type | User Role | Description |
| --- | --- | --- | --- |
| Referral Status Summary | Table, Pie Chart | PCP | Display "Number of Referrals" by Referral Status submitted by this PCP, for selected date range - system may display data for current month by default, including:<br>    Referral Status<br>    # of Referrals<br>    Percentage<br>* Clicking "Chart" icon may display the data in a pie chart format<br>* User may be able to switch between Table and Chart display<br>* Clicking "More. . ." may redirect user to the Report - Referral Status Report page, with more details displayed. |
| New Referral | Table | PCP Office Staff | Display new referrals submitted by this PCP Office Staff for the PCP Office, including:<br>    Referral #<br>    PCP<br>    Patient<br>    Specialty<br>    Specialist<br>    In/Out Network<br>* Clicking "More. . ." may redirect user to the Report - New Referral Report page, with more details displayed. |
| My Notifications | Table | PCP Office Staff | Display notifications sent to this PCP Office, including:<br>    Notification Date<br>    Notification Description |
| Referral Status Summary | Table, Pie Chart | PCP Office Staff | Display "Number of Referrals" by Referral Status submitted by this PCP Office Staff, for selected date range - system may display data for current month by default, including:<br>    Referral Status<br>    # of Referrals<br>    Percentage<br>* Clicking "Chart" icon may display the data in a pie chart format<br>* User may be able to switch between Table and Chart display<br>* Clicking "More. . ." may redirect user to the Report - Referral Status Report page, with more details displayed. |
| Healthcare System Referral Summary | Table | System Staff Admin | Display "Number of Referrals" categorized by Healthcare System, for selected date range - system may display data for current month by default, including:<br>    Healthcare System Name<br>    Total of Referrals<br>    In-Network Referrals #<br>    Leakage Referrals # |
| Leakage by Specialty/Specialist | Table | System Staff Admin | Display "Number of In-Network Referrals" and "Number of Leakage Referrals" by Specialty and Specialist, for selected date range - system may display data for current month by default, which also allows user to select All or One Healthcare System; for each Specialty, Total In- and Out- Network Referrals # may first be displayed, then for each Specialist, including:<br>    Specialty Name<br>    Specialist Last, First Name<br>    In-Network Referrals #<br>    Specialty Name<br>    Specialist Last, First Name<br>    Leakage Referrals #<br>* Clicking "More. . ." may redirect user to the Report - Leakage by Specialty/; Specialist Report page, with more details displayed. |
| Leakage Trend Summary | Column Chart | System Staff Admin | Display "Number of Leakage Referrals" by Year or Month, for selected Year/Month range in a column chart format for All or One Healthcare System, and All or One Specialty from the list; system may display "Number of Leakage Referrals" for current year for All Healthcare Systems and All Specialty in total. |

TABLE 26-continued

Dashboard - Dashlet Examples

| Dashlet Name | Type | User Role | Description |
| --- | --- | --- | --- |
| Top 10 Referral Healthcare System | Table | System Staff Admin | Display top 10 Healthcare Systems with the most Referrals submitted, for selected date range - system may display data for current month by default, including:<br>    Healthcare System Name<br>    # of Referrals |
| Top 10 Referral PCP | Table | System Staff Admin | Display top 10 PCP with the most Referrals submitted, for selected date range - system may display data for current month by default, including:<br>    PCP Name<br>    Healthcare System Name<br>    # of Referrals |
| Top 10 Referral Specialty | Table | System Staff Admin | Display top 10 Specialties that get referred for All or One Healthcare System, for selected date range, including:<br>    Specialty Name<br>    # of Referrals |
| Referral Status Summary | Table, Pie Chart | System Staff Admin | Display "Number of Referrals" by Referral Status for All or One Healthcare System from the list, for selected date range - system may display data for current month by default, including:<br>    Referral Status<br>    # of Referrals<br>    Percentage<br>* Clicking "Chart" icon may display the data in a pie chart format<br>* User may be able to switch between Table and Chart display<br>* Clicking "More. . ." may redirect user to the Report - Referral Status Report page, with more details displayed. |
| New Referral | Table | System Staff Admin | Display new referrals submitted in the system, which also allows user to select All or One Healthcare System from the Hospital list within the network, including:<br>    Healthcare System Name<br>    Referral #<br>    PCP<br>    Patient<br>    Specialty<br>    Specialist<br>    In/Out Network<br>* Clicking "More. . ." may redirect user to the Report - New Referral Report page, with more details displayed. |
| New Referral Assignment | Table | System Staff Admin | Display referrals that newly get assigned to Referral Coordinator, for All for One Healthcare System, including:<br>    Healthcare System Name<br>    Referral #<br>    Assigned By<br>    Assigned To<br>    Assigned Date |
| Legacy Referral | Table | System Staff Admin | Display referrals that have not been Closed for [X time period] since submitted, for All or One Healthcare System, including:<br>    Healthcare System Name<br>    Referral #<br>    Referral Status<br>    Assigned To<br>    Submitted Date<br>* Clicking "More. . ." may redirect user to the Report - Legacy Referral Report page, with more details displayed. |
| My Notifications | Table | Referral Coordinator Manager | Display notifications sent to this PCP, including:<br>    Notification Date<br>    Notification Description |
| New Referral | Table | Referral Coordinator Manager | Display new referrals for the assigned Healthcare System and Hospital, which allows user to select All or One Healthcare System from the assigned list and All or One Hospital from the assigned list, including: |

TABLE 26-continued

Dashboard - Dashlet Examples

| Dashlet Name | Type | User Role | Description |
| --- | --- | --- | --- |
| | | | Referral # |
| | | | PCP |
| | | | Patient |
| | | | Specialty |
| | | | Specialist |
| | | | In/Out Network |
| | | | * Clicking "More. . ." may redirect user to the Report - New Referral Report page, with more details displayed. |
| Referral Status Summary | Table, Pie Chart | Referral Coordinator Manager | Display "Number of Referrals" by Referral Status for All or One assigned Healthcare System/Hospital from the list, for selected date range - system may display data for current month by default, including: <br> Referral Status <br> # of Referrals <br> Percentage <br> * Clicking "Chart" icon may display the data in a pie chart format <br> * User may be able to switch between Table and Chart display <br> * Clicking "More. . ." may redirect user to the Report - Referral Status Report page, with more details displayed. |
| Legacy Referral | Table | Referral Coordinator Manager | Display referrals that have not been Closed for [X time period] since submitted, for All or One assigned Healthcare System/Hospital from the list, including: <br> Healthcare System Name <br> Referral # <br> Referral Status <br> Assigned To <br> Submitted Date <br> * Clicking "More. . ." may redirect user to the Report - Legacy Referral Report page, with more details displayed. |
| Referral Assignment Summary | Table | Referral Coordinator Manager | Display number of Referrals assigned by Referral Coordinator and Follow Up Coordinator that assigned with the same Healthcare System/Hospital, including: <br> Staff User Name <br> Staff User Role - Referral Coordinator or Follow Up Coordinator <br> # of Referrals assigned to |
| My Notifications | Table | Referral Coordinator | Display notifications sent to this PCP, including: <br> Notification Date <br> Notification Description |
| New Referral | Table | Referral Coordinator | Display new referrals for the assigned Healthcare System and Hospital, which allows user to select All or One Healthcare System from the assigned list and All or One Hospital from the assigned list, including: <br> Referral # <br> PCP <br> Patient <br> Specialty <br> Specialist <br> In/Out Network <br> * Clicking "More. . ." may redirect user to the Report - New Referral Report page, with more details displayed. |
| My Assignment | Table | Referral Coordinator | Display referrals that assigned to this user, including: <br> Referral # <br> PCP <br> Patient <br> Specialty <br> Specialist <br> Referral Status |
| My Notifications | Table | Follow Up Coordinator | Display notifications sent to this PCP, including: <br> Notification Date <br> Notification Description |
| New Referral | Table | Follow Up Coordinator | Display new referrals for the assigned Healthcare System and Hospital, which allows |

TABLE 26-continued

Dashboard - Dashlet Examples

| Dashlet Name | Type | User Role | Description |
|---|---|---|---|
| | | | user to select All or One Healthcare System from the assigned list and All or One Hospital from the assigned list, including:<br>　　Referral #<br>　　PCP<br>　　Patient<br>　　Specialty<br>　　Specialist<br>　　In/Out Network<br>* Clicking "More. . ." may redirect user to the Report - New Referral Report page, with more details displayed. |
| My Assignment | Table | Follow Up Coordinator | Display referrals that assigned to this user, including:<br>　　Referral #<br>　　PCP<br>　　Patient<br>　　Specialty<br>　　Specialist<br>　　Referral Status |

Embodiments comprise computer components and computer-implemented steps that will be apparent to those skilled in the art. For example, calculations and communications are performed electronically, and results can be displayed using a graphical user interface.

Figure 10:
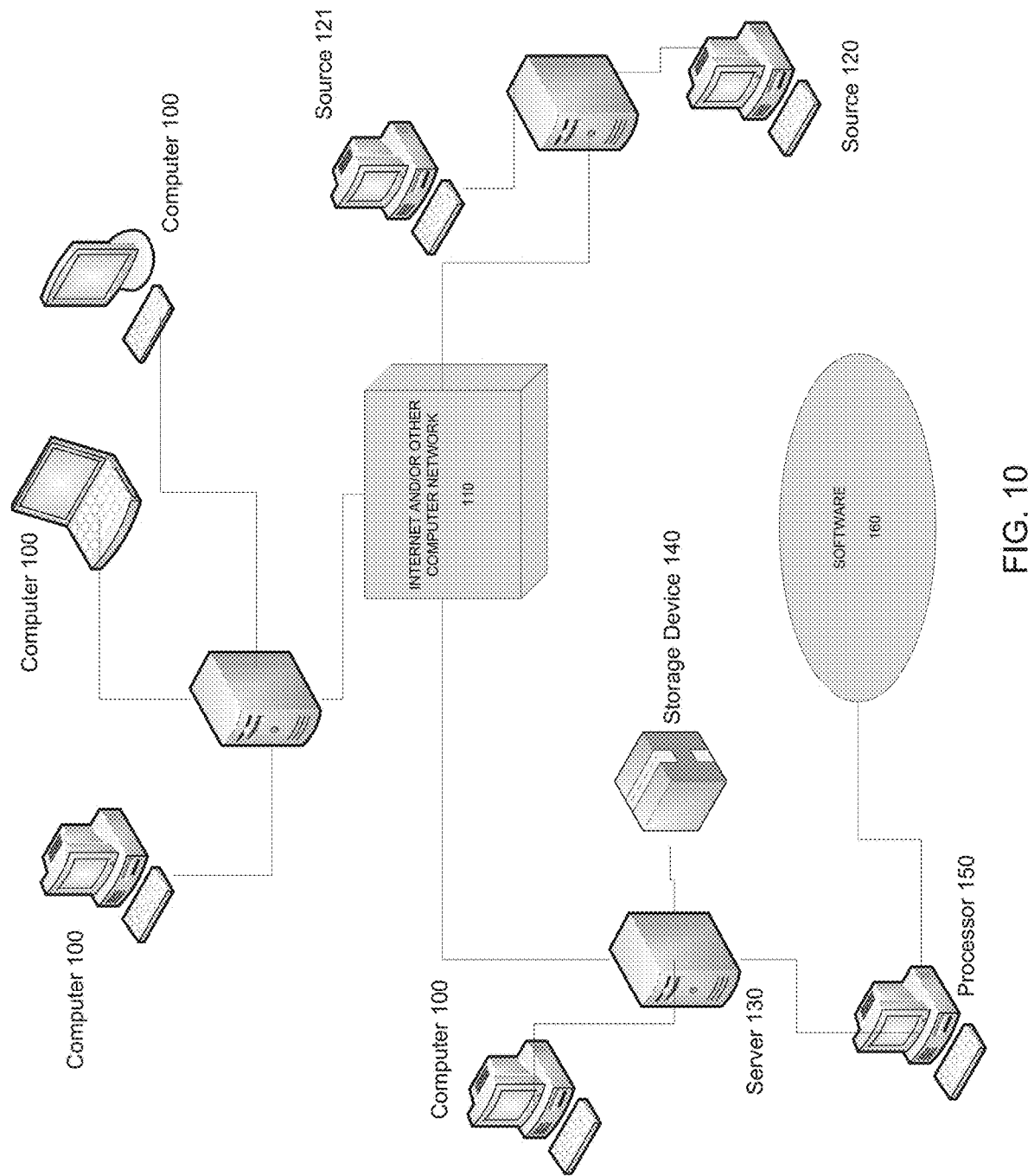
FIG. 10 is a block diagram of a computer system of an embodiment.

An exemplary such system is depicted in FIG. 10. Computers 100 communicate via network 110 with a server 130. A plurality of sources of data 120-121 also communicate via network 110 with a server 130, processor 150, and/or other components operable to calculate and/or transmit information. Server(s) 130 may be coupled to one or more storage devices 140, one or more processors 150, and software 160.

Calculations described herein, and equivalents, are, in exemplary embodiments, performed entirely electronically. Other components and combinations of components may also be used to support processing data or other calculations described herein as will be evident to one of skill in the art. Server 130 may facilitate communication of data from a storage device 140 to and from processor(s) 150, and communications to computers 100. Processor 150 may optionally include or communicate with local or networked storage (not shown) which may be used to store temporary or other information. Software 160 can be installed locally at a computer 100, processor 150 and/or centrally supported for facilitating calculations and applications.

For ease of exposition, not every step or element of the exemplary embodiments is explicitly described herein as part of a computer system, but those skilled in the art will recognize that each component, module, process, step, or element may have a corresponding computer system hardware component. Such computer system and/or software components are therefore enabled by describing their corresponding steps or elements (that is, their functionality), and are within the scope of the invention.

Moreover, where a computer system is described or claimed as having a processor for performing a particular function, it will be understood by those skilled in the art that such usage should not be interpreted to exclude systems where a single processor, for example, performs some or all of the tasks delegated to the various processors. That is, any combination of, or all of, the processors specified in the description and/or claims may be the same processor. All such combinations are within the scope of the invention.

Alternatively, or in combination, processing and decision-making may be performed by functionally equivalent circuits such as a digital signal processor circuit or an application specific integrated circuit.

FIG. 10 illustrates a block diagram of an example computer system that is suitable for use with exemplary embodiments. However, embodiments are operable in any of several computing environments that can include a variety of hardware, operating systems, and program modules. Program modules may include, but are not limited to, processors, routines, programs, components, data structures, and the like that perform particular tasks and/or implement particular data types.

Moreover, those skilled in the art will understand that embodiments may be practiced with other computer system configurations including, but not limited to, hand-held devices, network computers, multiprocessor based systems, microprocessor-based or other special purpose or proprietary programmable consumer electronics, minicomputers, mainframes, and the like. Exemplary embodiments may also be practiced in distributed computing environments where tasks are performed by remote processing devices that are linked through communications networks. In a distributed computing environment, program modules may be located in and/or executed from local and/or remote memory storage devices.

Exemplary embodiments and any other necessary programmed instructions and/or commands may be executable on processor 150. Processor 150 stores and/or retrieves programmed instructions and/or data from memory devices that can include, but are not limited to, Random Access Memory (RAM) and Read Only Memory (ROM) by way of a memory bus (not shown). User input to computer system 100 may be entered by way of a keyboard and/or pointing device. Human readable output from processor 150 may be viewed on an electronic display or in printed form on a local printer. Alternatively, processor 150 may be accessible by remote users for purposes that can include debugging, input, output and/or generating human readable displays in printed and/or display screen output form, or any other output form, by way of a Local Area Network (LAN) or Wide Area Network (WAN).

Many routine program elements, such as initialization of loops and variables and the use of temporary variables, are not described herein. Moreover, it will be appreciated by those of ordinary skill in the art that unless otherwise indicated, the particular sequence of steps described is illustrative only and can generally be varied without departing from the scope of the invention. Unless otherwise stated, the processes described herein are unordered—that is, the processes can be performed in any reasonable order.

The foregoing description relates to select exemplary embodiments. Those skilled in the art will understand that certain modifications may be made without departing from the spirit and scope of the invention.

Every document cited herein, including any cross referenced or related patent or application, is hereby incorporated herein by reference in its entirety unless expressly excluded or otherwise limited, The citation of any document is not an admission that it is prior art with respect to any invention disclosed or claimed herein or that it alone, or any combination with any other reference or references, teaches, suggests, or discloses any such invention. Further, to the extent conflicts with any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A computer system comprising:
   a client-side presentation layer processor;
   a server-side service layer component comprising at least one application programming interface (API) controller, at least one repository pattern processor, and a data layer processor; and
   a back-end layer component comprising at least one structured query language (SQL) server and a cache, wherein the client-side presentation layer processor provides leakage referral information, the leakage referral information including at least one of subspecialty information, date range information, hospital network information, healthcare network information, primary-care provider information, patient information, and subspecialty physician information that flags and identifies referrals that are requested outside of a healthcare network,
   wherein the client-side presentation layer processor analyzes referrals from a plurality of primary-care providers, generates a referral density pattern, generates a map based on the referral density pattern where referrals are directed and distances from the primary care providers to subspecialty physicians are illustrated, and analyzes geographic locations of the subspecialty physicians to associate the subspecialty physicians with at least one of the primary-care providers;
   wherein the referral density pattern is operable to provide the healthcare network with identified needs based on a number of referrals and distances for patients to travel,
   wherein the computer system provides at least one of the healthcare network and a hospital network with access to the referral density pattern and the geographic locations of subspecialty physicians for the at least one of the healthcare network and the hospital network to identify needs for the subspecialty physicians, and
   wherein the computer system generates a barcode and tracks referral coordination between the primary-care providers and the subspecialty physicians via the barcode, with each barcode representing a patient's progress in the referral.

2. The computer system as defined by claim 1, wherein the presentation layer processor comprises one or more controllers.

3. The computer system as defined by claim 1, wherein the one or more API controllers provide application security and authentication.

4. The computer system as defined by claim 1, wherein the data layer processor comprises at least one data access component.

5. The computer system as defined by claim 1, wherein the client-side presentation layer processor provides a secure portal that enables at least one of the primary-care providers to choose subspecialty referrals for the patients from a predetermined list of subspecialty physicians that are associated with at least one of the healthcare network and the hospital network.

6. The computer system as defined by claim 1, wherein the client-side presentation layer processor provides a secure portal that enables at least one of the primary-care providers to add a new subspecialty physician that is not included in at least one of the healthcare network and the hospital network, the new subspecialty physician being a leakage referral.

7. The computer system as defined by claim 1, wherein the client-side presentation layer processor provides an email notification to at least one of the primary-care providers, the email notification comprising information associated with a patient being admitted to at least one of an emergency department and a hospital.

8. The computer system as defined by claim 1, wherein the client-side presentation layer processor provides an email notification to at least one of the primary-care providers, the email notification comprising information associated with a patient being discharged from at least one of the hospital network and the healthcare network.

9. The computer system as defined by claim 1, wherein the client-side presentation layer processor provides a subspecialist consult report to a primary-care physician, the subspecialist consult report comprising information associated with a patient referral appointment.

10. The computer system as defined by claim 9, wherein the server-side service layer component tracks a date and time associated with the patient referral appointment, the server-side service layer component storing the date and time using the back-end layer component.

11. The computer system as defined by claim 9, wherein the client-side presentation layer processor automatically provides the subspecialist consult report to the primary-care physician in response to a patient at least one of missing the patient referral appointment, rescheduling the patient referral appointment, and cancelling the patient referral appointment.

12. The computer system as defined by claim 1, wherein the client-side presentation layer processor contacts a patient within a predetermined timeframe in response to the patient being discharged from at least one of an emergency department and a hospital.

13. The computer system as defined by claim 12, wherein a contact by the client-side presentation layer processor comprises scheduling a patient referral appointment.

14. The computer system as defined by claim 1, wherein the leakage referral information comprises a leakage referral trend analysis report.

* * * * *